(12) United States Patent
Tamayol et al.

(10) Patent No.: US 12,011,878 B2
(45) Date of Patent: Jun. 18, 2024

(54) MULTI-MATERIAL IN SITU BIOPRINTING

(71) Applicant: University Of Connecticut, Farmington, CT (US)

(72) Inventors: Ali Tamayol, Storrs, CT (US); Mohamadmahdi Samandari, Storrs, CT (US); Jacob Quint, Omaha, NE (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 17/570,431

(22) Filed: Jan. 7, 2022

(65) Prior Publication Data
US 2022/0212410 A1 Jul. 7, 2022

Related U.S. Application Data

(60) Provisional application No. 63/134,812, filed on Jan. 7, 2021.

(51) Int. Cl.
| | | |
|---|---|---|
| *B29C 64/336* | (2017.01) | |
| *B29C 48/02* | (2019.01) | |
| *B29C 64/118* | (2017.01) | |
| *B29C 64/209* | (2017.01) | |
| *B33Y 10/00* | (2015.01) | |
| *B33Y 30/00* | (2015.01) | |

(52) U.S. Cl.
CPC .......... *B29C 64/336* (2017.08); *B29C 48/02* (2019.02); *B29C 64/118* (2017.08); *B29C 64/209* (2017.08); *B33Y 10/00* (2014.12); *B33Y 30/00* (2014.12)

(58) Field of Classification Search
CPC ..... B29C 64/118; B29C 64/209; B33Y 10/00; B33Y 30/00
See application file for complete search history.

(56) References Cited

U.S. PATENT DOCUMENTS

| | | | |
|---|---|---|---|
| 2018/0056004 A1* | 3/2018 | Gamliel | A61M 5/46 |
| 2019/0009274 A1* | 1/2019 | Novak | G01N 33/5088 |
| 2020/0130277 A1* | 4/2020 | Thorpe | B29C 64/209 |
| 2020/0270555 A1* | 8/2020 | Ingber | C12M 23/34 |
| 2021/0039306 A1* | 2/2021 | Busbee | B29C 64/209 |
| 2022/0410094 A1* | 12/2022 | Zhu | B29B 7/72 |

FOREIGN PATENT DOCUMENTS

CN 110450407 A * 11/2019

* cited by examiner

*Primary Examiner* — Farah Taufiq
(74) *Attorney, Agent, or Firm* — Ballard Spahr LLP

(57) ABSTRACT

A multi-material printer can include a housing that is configured to be handheld. The housing can be configured to receive first and second printable materials from respective first and second containers. A nozzle can define an outlet of the multi-material printer. At least one actuator can be configured to cause first and second printable materials from the first and second containers to flow at a respective constant rate. The multi-material printer can be configured to simultaneously extrude the first and second printable materials from the outlet. The multi-material printer can be used for fabricating a scaffold from filaments comprising the first and second materials directly within the body of a human or animal.

19 Claims, 14 Drawing Sheets

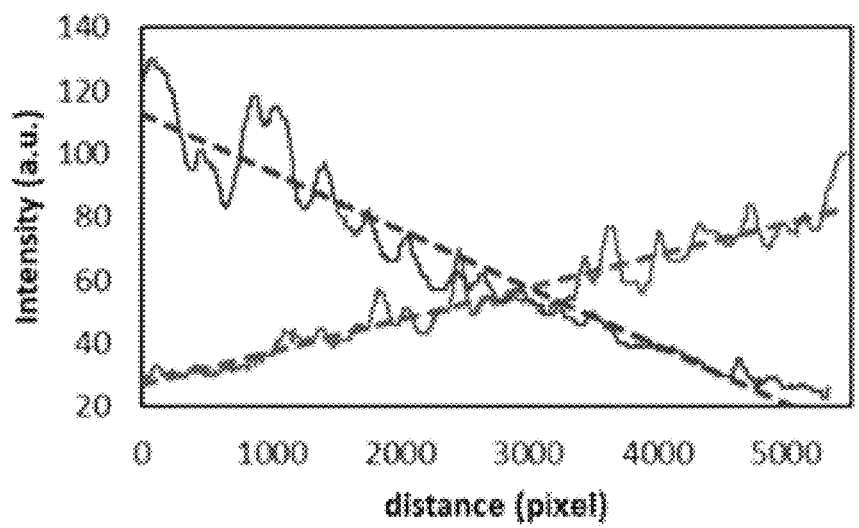
FIG. 9C
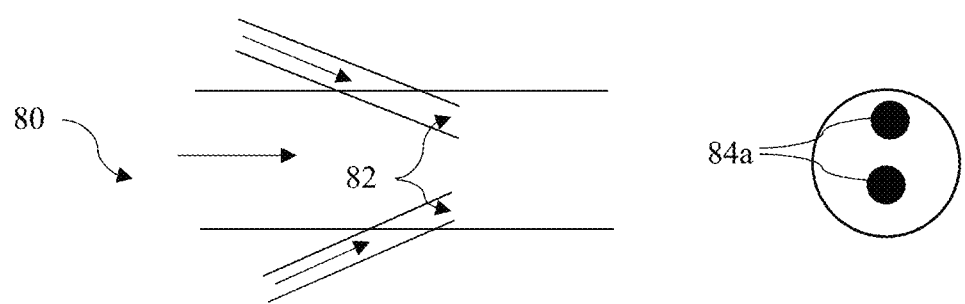
FIG. 10A
FIG. 10B

MULTI-MATERIAL IN SITU BIOPRINTING

CROSS-REFERENCE TO RELATED APPLICATIONS

This application claims priority to and the benefit of the filing date of U.S. Provisional Patent Application No. 63/134,812, filed Jan. 7, 2021, the entirety of which is hereby incorporated by reference herein.

FIELD

This disclosure relates to bioprinting and, in particular to multi-material bioprinters that can print in situ and methods of use of such multi-material bioprinters.

BACKGROUND

Biomaterials have been injected into injury sites, but conventional means for injecting biomaterials fail to control any spatial organization of the delivered material. Moreover, conventional means are limited to single materials. Traditionally, bioprinted constructs are printed outside of the body and implanted into the body. However, implantation of soft scaffolding is different and requires some form of fixation: adhesion to a suturable scaffolding material or the use of adhesives. These fixation modes fail to match the local wound structure. Recently, some research groups have attempted to print within the body, called in situ bioprinting. However, creating scaffolds from hydrogels directly inside the body of a patient is not trivial, and the use of single-material bioprinters limits the effectiveness of these devices. Injuries typically involve multiple tissues and require multiple materials, cells, regenerative factors, chemical and physical properties, and different architectures. Furthermore, proper integration requires proper adoption and remodeling of the implanted scaffold based on the in vivo environmental stimuli required for regeneration and functional recovery of the tissue. A notable example is a need for vascularization, which can be addressed by in situ printing of multicompartmental filaments forming capillaries upon exposure to body temperature.

Existing technologies fail to deliver spatial control of multiple materials at the site of injury using a portable tool. Existing technologies further fail to enable the controlled mixing and spatial pattern control over the precursor material in a translatable handheld device. The resolution of extrusion-based printers is not high enough for many tissue engineering applications. Control over the features within each extruded filament increases the resolution beyond current limitations to the extent that is needed to recapitulate physiologically detailed features like vascular, neural, and lymph tissues. As further disclosed herein, the described bioprinters and bioprinting systems and methods can address these and other deficiencies of existing technologies.

SUMMARY

Described herein, in various aspects, is a bioprinter that can be or comprise a handheld device. The bioprinter can comprise a pen printer. The bioprinter can be easily operated using simple mechanical controls to extrude polymer precursors at a consistent rate. This flow can be customized to the desired flow rate. Polymer precursors can first be loaded into syringes and placed into the bioprinter (e.g., pen printer), where they can then be extruded using actuators (e.g., electrical actuators). The actuators can accurately push the plunger of the syringe towards the outlet (e.g., front) of the syringe, extruding the polymers out. Because the polymers are loaded into standard syringes, the nozzle of the syringe can be optimized to the polymer being used, using standard needles or tapered nozzles with any gauge size. While the disclosed bioprinter and bioprinting methods can be used with a wide range of polymers, some exemplary materials that can be extruded by the bioprinter include hydrogels. The handheld bioprinter can accommodate two or more syringes. A mixing technology, as further disclosed herein, can allow the fabrication of fibers from single or multiple materials with designed architectures. When sacrificial materials are used as one of the extruded components, fibers with embedded capillaries/cavities can be generated. The disclosed handheld bioprinter can allow for the fabrication of scaffolds with different compartments, which can optionally carry distinct materials, biological factors, and/or cells.

The multi-material handheld bioprinter can be used in research and teaching institutions as well as in many medical applications including, but not limited to, the treatment of skin injuries, wounds, and/or burns, the reconstruction of cancer dissection sites, or the treatment of muscle injuries, bone loss, and/or cardiac defects.

In one aspect, a multi-material printer can comprise a housing that is configured to be handheld. The housing can be to receive first and second printable materials from respective first and second containers. A nozzle can be in communication with the housing. The nozzle can define an outlet of the multi-material printer. At least one actuator that can be configured to cause the first and second printable materials from the first and second containers to flow through the housing at a respective controlled rate. The multi-material printer can be configured to simultaneously extrude the first and second printable materials from the outlet.

In one aspect, a method can comprise extruding, from first and second containers, first and second biomaterials. A mixer can mix the first and second biomaterials to form a mixture having a predetermined cross sectional structure. The mixture can be extruded through a nozzle to form a filament.

Additional advantages of the disclosed bioprinter and bioprinting systems and methods will be set forth in part in the description that follows, and in part will be obvious from the description, or may be learned by practice of the claimed invention. The advantages of the disclosed bioprinter and bioprinting systems and methods will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIG. 9C illustrates pixel intensity quantification across the length of the fiber to demonstrate the continuous gradient.

FIG. 10A illustrates a mixer for forming a fiber. FIG. 10B depicts an exemplary profile of a fiber formed by the mixer shown in FIG. 10A.

DETAILED DESCRIPTION

Figure 1:
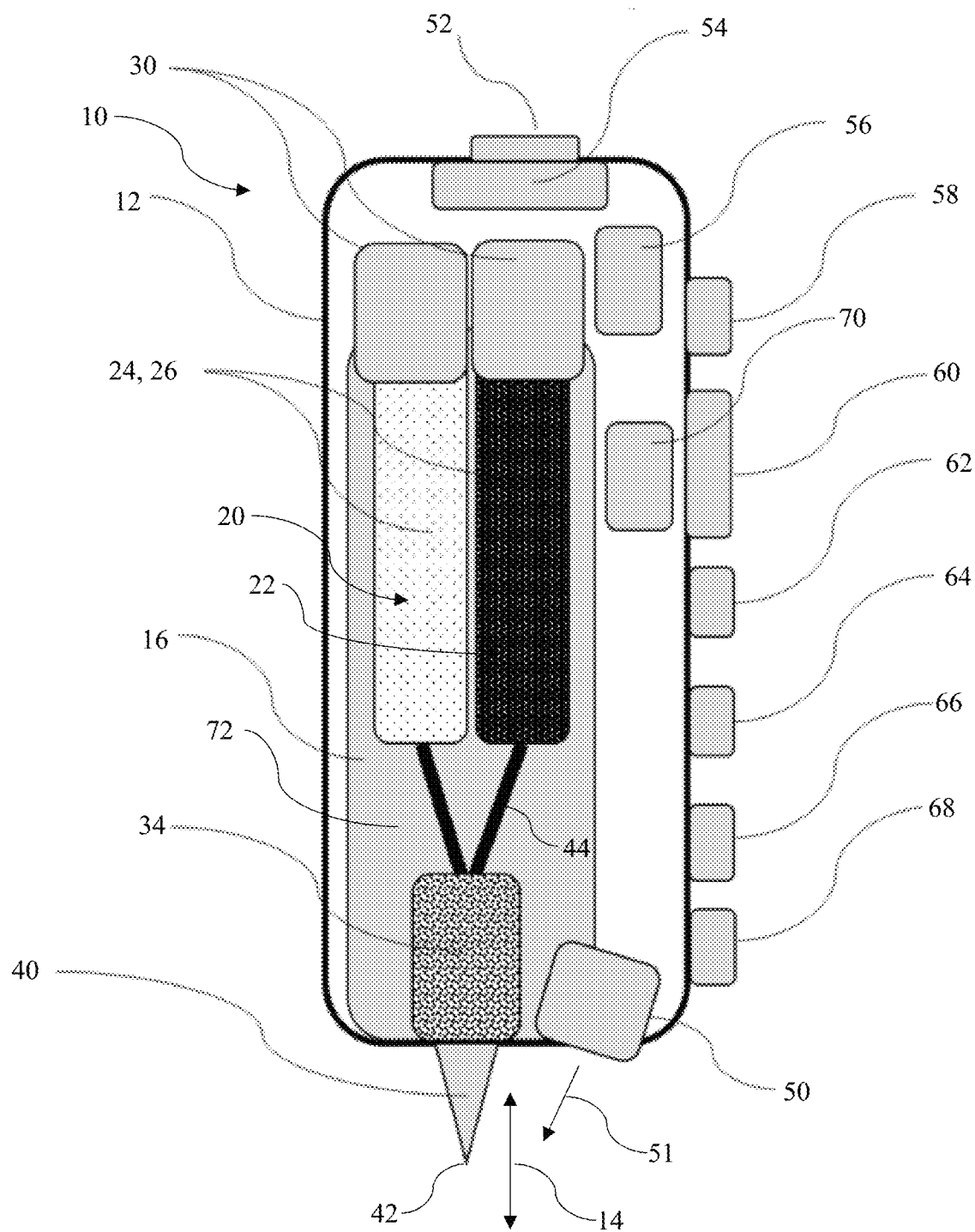
FIG. 1 is a schematic diagram of an exemplary handheld material bioprinter as disclosed herein.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a syringe" can refer to one or more of such syringes, and so forth.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, in some optional aspects, when values are approximated by use of the terms "substantially" or "generally," it is contemplated that values within up to 15%, up to 10%, up to 5%, or up to 1% (above or below) of the particular value can be included within the scope of those aspects. When used with respect to an identified property or circumstance, "substantially" or "generally" can refer to a degree of deviation that is sufficiently small so as to not measurably detract from the identified property or circumstance, and the exact degree of deviation allowable may in some cases depend on the specific context.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

The word "or" as used herein means any one member of a particular list and, unless context dictates otherwise, can also include any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

In the past decade, bioprinting has emerged as a technology that can create highly organized tissue constructs that mimic the complex architecture of various organs. Three-dimensional (3D) bioprinters are capable of printing both hard and soft polymers. The scaffolds that are 3D printed for the engineering of soft tissue are typically hydrogel-based. Despite the impressive level of the structural details achievable with 3D bioprinters, the implantation of hydrogel-based constructs has remained a major rate-limiting step. Hydrogels are not suturable and, once fabricated, do not adhere properly to tissues. Moreover, conventional 3D bioprinters are slow in responding to urgent clinical needs. For example, in the case of a traumatic injury, it takes several hours to take 3D images from the injury site and construct a 3D file (e.g., a Standard Tessellation Language (STL) file) that can be used with a conventional 3D printer. The printing process on its own takes several hours. Thus, by the time the construct is ready, the patient has already gone through surgical procedures and the implantation of the scaffold requires secondary surgery. Further, the reduction of the need of 3D imaging removes the discrepancies from the injury or defect at the time of imaging and at the time of treatment due to debridement, motion of the wound, disease or defect progression, amputation, surgical resection of unpredicted margins, or any other change from the predicted tissue reconstruction.

The bioprinter disclosed herein can print photocrosslinkable hydrogels such as GelMA in situ at the time of injury (or shortly thereafter). This can eliminate the need for a second surgery. It is further contemplated that the in situ printing of adhesive hydrogels as disclosed herein can solve the challenge of implantation of hydrogel-based scaffolds.

The disclosed bioprinter can revolutionize the use of 3D bioprinters in surgical procedures. The disclosed bioprinter is robust and can be used in any place and in any setting without the need of accessing an expensive imaging modality.

In use, the clinician (e.g., surgeon) can inspect the application area (e.g., a defect area), adjust the printing rate based on the application area and other patient needs, and print material into the application area (e.g., fill the defect area). The in situ printing and crosslinking can enhance the adhesion of the material to the surrounding tissue, thereby eliminating the risk of scaffold slippage. The use of multiple materials enables the construction of physiologically relevant tissues.

Multi-material printing can be highly crucial for the proper treatment of volumetric defects in various tissues or in cases of polytrauma where multiple tissues are injured. The use (and printing) of multiple materials enables the construction of physiologically relevant tissues. The spatial control over the composition of the depositing bio-ink both across and along the filament offers the ability to recreate more complex structures and tissues than are available with currently available extrusion or material jetting additive manufacturing (3D printing) systems. Thus, the disclosed systems and methods allow for controlling the physical and chemical properties of the scaffold with resolution comparable to native tissue structures, to better tune the scaffold for enhanced regeneration. The ability to integrate multiple materials and refine the resolution of bioprinting can save money and increase the types of tissues that can be treated with in situ printers. Furthermore, controlling the interaction between different materials to be printed and their response to in vivo physical and chemical stimuli in such sub-filament resolution further enables the formation of scaffolds beyond the capability of other bioprinters. Recreating the interface between various tissues requires creating precise gradients at short length scales and that can only be achievable by having sub-filament resolution in a way that the position of multiple materials and their concentrations can be controlled at the nozzle. The disclosed bioprinting systems and methods can take advantage of physical and chemical cues generated inside the filaments for an improved regeneration rate and an improved quality of regeneration.

The handheld bioprinter can allow for the fabrication of scaffolds. In some aspects, the scaffolds can comprise one or more compartments. Such compartments can optionally carry distinct materials, biological factors, and/or cells. Embodiments disclosed herein can be used to print multiple materials from a single device; form fibers with multiple distinct compartments; and/or fabricate scaffolds in which every single fiber has embedded capillaries (e.g., microcapillaries) with adjustable size.

In situ printing can eliminate treatment delays and can create customized scaffolds to accommodate specific tissue defects.

Disclosed herein is a multi-material handheld bioprinter that can be used to print materials (e.g., polymers, biomaterials, etc.) for in situ applications. In some aspects, the multi-material handheld bioprinter can include a housing 12, material precursor storage containers 24, 26, environmental controls 16, an extruding mechanism 30, a mixer (e.g., a static mixer) 34, a nozzle 40, and external crosslinking mechanism 50. The multi-material handheld bioprinter can be easily operated using simple electrical and mechanical controls to extrude different materials at a regulated rate. Extrusion can be customized to the desired flow rate. The printable materials (e.g., polymer precursors) can be loaded into the material storage containers 24, 26. The material storage containers can be positioned within the handheld bioprinter. The materials within the storage containers can be extruded into the mixer using actuators 30 (e.g., electrical actuators). The actuators 30 can cause extrusion/intrusion through mechanical displacement or pneumatic pressure. The multi-material precursors can be extruded into the mixer 34 and mixed to varying levels or in various arrangements to form various architectures. The mixer can be provided as an adapter (e.g., a separate component that is coupled to the housing 12). Thus, a particular mixer can be selected based on a desired mixing profile and can be coupled to the housing to adapt the printer for a particular application. The mixer can be configured to control the degree of mixing and spatial organization of precursor materials across the printing filament (e.g., in a cross section transverse to an outlet of the nozzle 40). Modulation of the flow rate and integration of the mixing module can further allow real-time control of filament deposition along with the fiber. The nozzle 40 can control the applied stress to the material and shape of the filament upon deposition.

The nozzle 40 of the printer can be optimized for use with the polymer (or combination of polymers) being used. Optionally, the nozzle can be embodied by a standard needle and tapered nozzle with any suitable gauge size. In further aspects, the nozzle can be custom-built with an inlet (e.g., a circular inlet) and any desired outlet profile. The handheld bioprinter can accommodate (e.g., receive therein) two or more syringes with printable material therein. In some aspects, the mixer can be used to fabricate fibers from single or multiple materials with designed architectures. Each material can carry different components such as cells, particles, and/or chemical reagents. The materials can interact with each other upon interfacing, or be affected by external stimuli upon printing, inducing a chemical or physical change in the filament. A notable example is the use of sacrificial materials (e.g., materials that can be removed as further disclosed herein) as one of the components, which forms fibers with embedded capillaries (e.g., microcapillaries). In exemplary aspects, the filament can have an axis of elongation, and the capillaries can have cross-sectional dimensions (e.g., a diameter) transverse to the filament axis of elongation that can range from nanometers to micrometers (such capillaries being referred to herein as "microcapillaries"). For example, the capillaries can have cross sectional dimensions from about 10 nm to about 100 micrometers, or from about 50 nm to about 50 micrometers, or from about 100 nm to about 10 micrometers.

Disclosed herein, in various aspects, and with reference to FIGS. 1-6, is a multi-material handheld printer 10. The multi-material handheld printer 10 can be configured to print a filament 11. In further aspects, the multi-material handheld printer 10 can be configured to print droplets. The multi-material handheld printer 10 can be used to fabricate scaffolds with sub-filament features. These sub-filament features can be formed by one or more different material concentrations, a different number of linear compartments, a different number of coaxial compartments, varying internal geometries, or different discrete or continuous gradients. The sub-filament control over material position and architecture can enable the formation of physiologically relevant tissue-like scaffolds. After printing, some materials can be dissolved (or otherwise removed) to create sub-filament compartments. In some aspects, the scaffolds can be formed with one or more compartments therein. The compartments can serve as topological cues for cells. For example, the compartments can define architectural features to allow for the recapitulation of lymph, nervous, or vascular networks, different tissue layers, etc. In exemplary aspects, a filament or filament subunit (e.g., drop) can be configured to form linear and/or radial compartments.

The multi-material handheld printer 10 can comprise a housing 12 that is configured (e.g., sized and shaped) to be handheld. That is, the housing 12 can be sized and configured to fit in a user's hand and suitably shaped to allow for manipulation like a pen or pencil. Accordingly, the printer can be a pen printer. Accordingly, at least a portion of the multi-material handheld printer can be held and controlled via the movement of the operator's hand, and the spatial deposition of the extruded filament can be controlled via manual displacement of the operator's hand.

In exemplary aspects, the housing 12 can have a longitudinal axis 14 and cross sections perpendicular to the longitudinal axis. The cross sections of the housing can optionally have a major dimension no greater than 3 inches, or no greater than 2 inches. In various aspects, the cross sections can be oblong, having a length of less than 2 inches (e.g., from about 1 inch to about 2 inches, or about 1.5 inches) and a width of less than 1 inch (e.g., from about 0.5 inches to 1 inch). In some optional aspects, the printer 10, or the handheld portion thereof, can weigh less than 450 grams, or less than 400 grams, or less than 350 grams.

The multi-material handheld printer 10 can be configured to receive at least a first printable material 20 and a second printable material 22 (e.g., precursor materials). For example, the first and second printable materials 20, 22 can be provided in respective cartridges 24, 26 or other suitable containers. Optionally, the respective cartridges 24, 26 can be integrally formed with each other, with divided interior volumes to receive the first and second printable materials 20, 22. In further aspects, the respective cartridges 24, 26 of the first and second printable materials can be separate elements. Optionally, cartridges 24, 26 of the first and second printable materials can be separate elements that can be coupled together (e.g., by receipt within the housing 12 housing). The first and second cartridges 24, 26 can be configured to be at least partially (optionally, entirely) received within a cavity 16 defined by the housing 12 (or a plurality of cavities to receive respective cartridges). Accordingly, in some aspects, an entirety of the printer 10 can be handheld. In still further aspects, the first and second or more printable materials 20, 22 can be stored in remote containers and can be provided to the housing via respective flexible conduits 44.

In some optional aspects, the multi-material handheld printer 10 can be configured to receive at least three materials. For example, the cavity 16 defined by the housing 12 can simultaneously receive three, four, five or more containers having printable materials therein. Optionally, in these aspects, it is contemplated that the printer can simultaneously print three or more materials. In further aspects, the printer can enable the selection of only a subset of the specific materials among the various materials that are to be printed (optionally, simultaneous printed) during a given procedure. For example, when three materials are provided, it is contemplated that the printer 10 can permit printing of a single one of the materials, simultaneous printing of two of the materials, or simultaneous printing of all three materials. In exemplary aspects, the rate of the extrusion of each material can be individually controlled.

One or both of the first and second printable materials (or all of the printable materials in embodiments comprising three or more printable materials) can be biomaterials. At least one of the first material and the second printable material can be a hydrogel. Optionally, at least one of the first material or the second material can comprise a cross-linking agent. Optionally, one of the first material or the second material can be a sacrificial material. For example, one material can comprise gelatin that can be removed to leave behind compartments (e.g., capillaries) as further disclosed herein. Sacrificial materials can be removed during or after the printing process through thermal incubation, diffusion, aspiration, dissolving, or other means. In some exemplary aspects, one or both of the first and second printable materials can comprise photocrosslinkable hydrogels, such as gelatin methacryloyl (GelMA). In further aspects, the biomaterials (e.g., the first printable material, the second printable material, and any additional printable materials) can comprise one or more of a polymer, a protein, nucleic acids, lipids, ceramic, mixture, or other biomaterials. Optionally, in these aspects, the printable material can comprise any polymer such as, for example and without limitation, polycaprolactone, polylactic acid, poly glucolic acid and their co-polymers, alginate, chitosan, etc., or one or more proteins (e.g., collagen or gelatin, or a combination thereof), or combinations thereof. The polymer(s), protein(s) or their mixtures can be functionalized with different chemicals and chemistries. The polymer(s) or their mixture or protein(s) and their mixtures can be mixed with nanoparticles of any shape or microparticles of any shape made or chemicals made from any material composition. Examples include metal (silver, gold, magnesium, zinc, selenium, etc), metal oxides, metal peroxides, bioglasses, radiopaque agents, antibacterial compounds and agents, antimicrobial compounds and agents, antibiotics, bioceramics, ceramics, oxygen generating materials, crosslinking agents, proteins, vitamins, lipids, phospholipids, fatty acids, biological factors, polysaccharides, nucleic acids, growth factors, hydroxyapetite, calcium phosphate, carbon nanotubes, quaternary ammonium compounds, graphene, graphene oxide, carbon derived materials, liquid crystals, peptides, chitosan, silver nitride, platelet rich plasma, bone marrow-derived materials, pain killers, anti-inflammatory drugs or reagents, blood-derived materials and their combinations, etc. The concentrations of the nanoparticles or microparticles or chemicals can be of any suitable range. Each material can comprise different components such as cells, particles, biological compounds, and/or chemical reagents. The materials can interact with each other upon interfacing, or be affected by external stimuli upon printing, inducing a chemical or physical change in the filament. For example, in various aspects, the biomaterials can crosslink, form secondary structures, form foam, form a gas, or cause destructive or constructive interference. In some aspects, the printed materials can form a filament having two or more different cell types, or growth factors mixed or disposed in distinct regions of the filament.

The multi-material handheld printer 10 can comprise at least one actuator 30 that is configured to force the first and second materials toward an outlet of the printer. In some aspects, the at least one actuator 30 can be configured to cause the first and second materials to flow through the housing at a controlled constant or variable rate (e.g., a constant or variable volumetric flow rate). For example, the cartridges 24, 26 can be syringes that can output the first and second printable materials 20, 22 upon linear movement of a respective plunger 32 along a respective longitudinal axis 31 of the cartridge. In some aspects, the plungers 32 can be actuated by a single linear actuator 30. In further aspects, a respective actuator 30 can be configured to independently actuate each plunger 32. The actuator(s) 30 can optionally be electromechanical. The actuator(s) 30 can be configured to operate at selectable speeds to control an output rate of the printed materials (e.g., the first and second materials 20, 22) of the multi-material handheld printer 10. The actuator(s) 30 can optionally be direction reversible. In this way, the actuator(s) 30 can be actuated to retract to receive a full cartridge. The actuators(s) 30 can optionally be electromechanical actuators. In various aspects, the actuators 30 can use direct contact with the material to extrude the material (e.g, via a plunger), apply a pneumatic pressure to the material, or effect movement of the material via screw rotation.

In some aspects, the printer 10 can have a first actuator that is configured to effect flow from the first container and a second actuator that is configured to effect flow from the second container. In aspects comprising three or more containers, a respective actuator can be configured to effect flow from each container. Optionally, a relative flow rate of the first material to the flow rate of the second or more materials can be varied to vary a ratio of the first material to the second or more materials along the length of a printed filament.

Referring to FIGS. 1-5, the multi-material handheld printer 10 can comprise a nozzle 40 in communication with the housing 12. Optionally, the nozzle 40 can be integral to the housing 12. In further aspects, the nozzle can be removably coupled to the housing 12. The nozzle 40 can define an outlet 42 of the multi-material handheld printer 10. The outlet 42 can have a cross section that defines the shape of the outer perimeter of a filament printed by the multi-material handheld printer 10. For example, the outlet 42 can have a cross sectional profile of a circle, oval, square, rectangle, trapezoid, triangle, or any shape or any array of shapes. The nozzle 40 can optionally define a taper toward the outlet 42. Different filament profiles can be used in the printing of scaffolds with different resolutions, volumes, and cross-sectional shapes. For example, for a burn wound which usually involves a large skin area, rapid printing of sheets covering the wound is required, while for treatment of volumetric muscle loss, a circular profile with good resolution is necessary to recapitulate the native muscle structure and fill the complex irregular-shape cavity.

The multi-material handheld printer 10 can comprise a mixer 34 (e.g., a static mixer). The mixer 34 can be configured to shape the first printable material and the second printable material (and any further printable materials). For example, referring also to FIGS. 4A and 4B, the mixer can (optionally, with further control of the deposit rates of the actuators 30) control output ratios of the first printable material to the second printable material (and any further printable materials) to adjust the material composition. Still further, as further described herein, the first and second printable materials can be printed to form one or more compartments (linear and/or coaxial) within a filament, and the mixer 34 can, at least in part, determine the number of compartments across the filament. For example, a first exemplary cross-sectional profile 90 can have a pair of linear compartments 84. A second exemplary cross-sectional profile 92 can have several (e.g., about 20) linear compartments. A third exemplary cross-sectional profile 94 can have a single circular compartment 84. A fourth exemplary cross-sectional profile 96 can have a plurality of circular compartments 84. In further aspects, the mixer 34 can be configured to mix the first and second printable materials (and any further printable materials). Optionally, the mixer 34 can be configured to mix the first and second printable materials (and any further printable materials) at a ratio that changes (or respective ratios that change) across a cross section of the material as it leaves the nozzle 40.

Figure 11A:
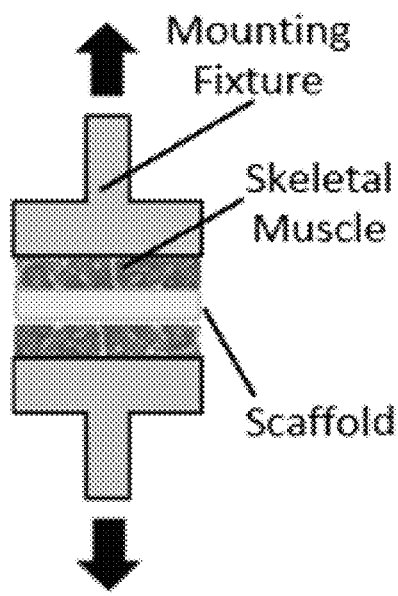
FIG. 11A shows an exemplary structure of in situ printed GelMA undergoing tensile forces.
Figure 11B:
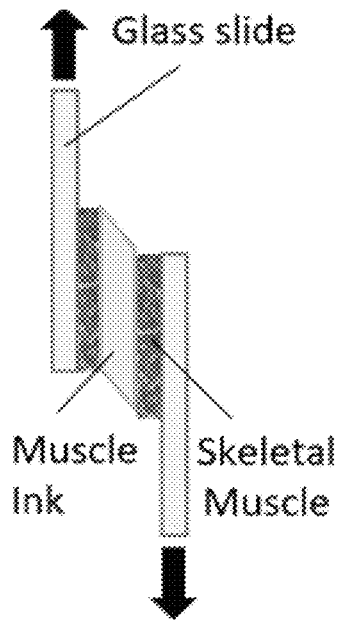
FIG. 11B shows test results of adhesion stress.
Figure 11C:
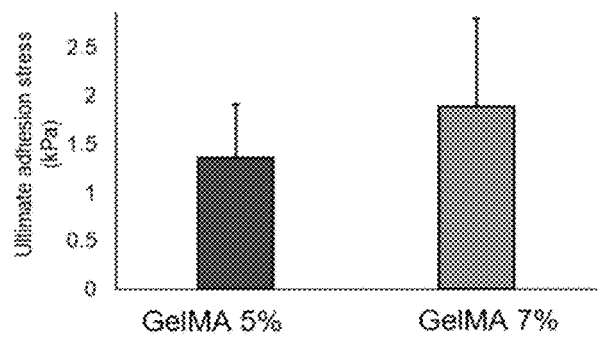
FIG. 11C shows an exemplary structure of in situ printed GelMA undergoing shear forces.

In exemplary aspects, and as shown in FIGS. 6A and 11A-11C, the mixer can comprise one or more helical mixing elements 86 that are configured to divide the flow of material into two streams, rotate the streams, and interface said two streams in reverse order, as further described herein. The helical mixing elements can have a generally helicoid shape (e.g., a flat material with an intermediate 180 degree twist between opposite ends of the material). The helical mixing elements 86 can be axially spaced and rotationally offset from each other (e.g., with sequential mixing elements 86 being rotationally offset by 90 degrees or about 90 degrees as shown in FIG. 11C).

In some optional aspects, the nozzle 40 and mixer 34 can be provided as a unitary, monolithic component. In further aspects, the nozzle 40 and mixer 34 can be separate components that are coupled together (and, in exemplary aspects, capable of being selectively decoupled from one another).

The mixer 34 can be configured to couple to the housing 12 via a union such as, for example, a LUER-LOCK fitting. For example, the housing 12 can comprise a female fitting 48 that is configured to receive a male fitting 46 of the mixer 34. The housing can comprise respective channels that extend between and provide fluid communication between the material containers and the mixer 34. The channels 44 can have narrow cross sections (e.g., having a cross-sectional diameter of greater than 2 μm and less than 2 mm) to ensure laminar or substantially laminar flow therein while minimizing the shear stress applied to the precursor materials, as the reduction in shear stress can reduce adverse effects on encapsulated cells.

In some optional aspects, the multi-material handheld printer 10 can comprise a radiation source 50 for emitting an electromagnetic radiation (e.g., visible light, infrared light, or ultraviolet (UV) light) for crosslinking the printed materials. For example, the radiation source 50 can be an FDA-approved light source used in dentistry, emitting a wavelength of about 420 nm). The radiation source 50 can be integral to the housing 12. The radiation source 50 can optionally be configured to emit along an emission axis 51. The emission axis can be oriented relative to the nozzle so that light from the radiation source is incident on material that is exiting the nozzle. The radiation source 50 can be connected to a power source 52. The intensity of the radiation source can be controlled via an actuator 68. The radiation source 50 can be directed to pre-extruded materials in the nozzle 40 or at the deposited filament 11 (e.g., at, or adjacent to the outlet 42). In further aspects, the radiation source can also be derived from multiple locations on the printer or in a continuous loop around the nozzle 40. The radiation source 50 can be manipulated by lenses or optical fibers to vary the exposure pattern.

The multi-material handheld printer 10 can comprise a power source 52. Optionally, the power source 52 can comprise a power input socket that is configured to receive a power cable connector. In further aspects, the power source 52 can be an integral power cord. In further optional aspects, the multi-material handheld printer 10 can comprise a battery 54 that is configured to receive power from the power source 52. The power source can comprise a direct or inductive power source. Optionally, the extrusion power of the device can be manually powered by an applied force from the operator.

In some optional aspects, the multi-material handheld printer 10 can comprise a ultrasonic source for emitting sound waves to manipulate the biomaterial or its constituents at any point of the extrusion process (e.g., at the outlet 42, or at a portion of the filament that has exited the outlet and is spaced from the outlet). In further optional aspects, the multi-material handheld printer 10 can comprise an emission source that is configured to emit chemical, ionic, physical, or enzymatic agents at any point of the extrusion process to aid in disinfection, crosslinking, generation of internal or external geometries, or other features.

In further optional aspects, the multi-material handheld printer 10 can comprise a thermal emission source that is configured to heat the air around the extruded filament or subunit at the point of extrusion process to aid in crosslinking, reduction in contamination, removal of temperature-sensitive materials, etc.

The multi-material handheld printer 10 can comprise a microcontroller 56, a logic board, or other memory and coupled processor(s) for monitoring and controlling one or more aspects of the multi-material handheld printer further disclosed herein. The multi-material handheld printer 10 can optionally comprise a power control 58 (e.g., an on/off switch). The multi-material handheld printer 10 can comprise a display 60 (e.g., an LCD display) that is configured to display one information associated with the printer. The display can display, for example, one or more of the materials loaded within the printer, material properties, the volume of materials remaining or used, climate control information (temperature, humidity, etc.), linear, volumetric, and relative flow rates, input pressures and forces, battery power, and/or radiative information (intensity, flux, wavelength, etc.). The display can further be a touchscreen that can receive user input.

The multi-material handheld printer 10 can be configured to permit user control over the power of the device, deposition rate, deposition actuator direction, deposition application, radiative crosslinking intensity, radiative crosslinking application, and temperature control. Accordingly, the multi-material handheld printer 10 can comprise one or more input devices (e.g., knobs, buttons, slides, switches, a touch screen, etc.) that are configured to control one or more one more aspects of the printer. For example, the multi-material handled printer can comprise one or more of: a deposition control rate input device 62 that adjusts the rate at which the actuator(s) 30 move; an actuation direction input device 64 (e.g., a switch that determines movement direction of the actuator(s) 30; a deposition power control 66 (e.g., a button that starts and stops movement of the actuator(s); and/or a control input device for controlling the radiation source 50 (e.g., a switch that turns the radiation on and off and/or a knob that selects a desired output wavelength). The multi-material handheld printer 10 can comprise a transmitter 70 (e.g., a transceiver) that is configured to communicate with a remote computing device (e.g., to transmit programming and information to the remote computing device). The information that can be transmitted or received by the device can consist of processor logic to relate internal controls and the history of the settings of the device. The printer 10 can be programmed from received information to adjust the function of the input devices, the relation of any two or more input parameters, or any parameters of the extrusion (e.g., extrusion rate), temperature control, radiative, or mixing system. Controls for the actuator 30, for example buttons or other inputs (e.g., deposition power control 66), can be positioned to allow the user to actuate the actuator while holding the printer 10 like a pen during use.

In some aspects, the printer 10 can comprise a temperature control system 72 that maintains the printable materials at a set temperature. The temperature control system 72 can comprise, for example, a heater, a temperature sensor (e.g., a thermocouple or thermistor), and a microcontroller for adjusting the heater based on temperature sensed by the temperature sensor. Optionally, the set temperature can be set by an input device of the printer 10. For example, the temperature control system can maintain the proper temperature of the precursor materials to maintain their rheological and biological properties.

Mixer

Figure 6A:
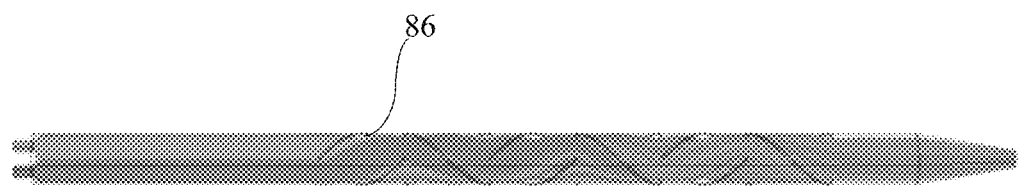
FIG. 6A shows an exemplary distribution of materials within an exemplary static mixer as disclosed herein.
Figure 6B:
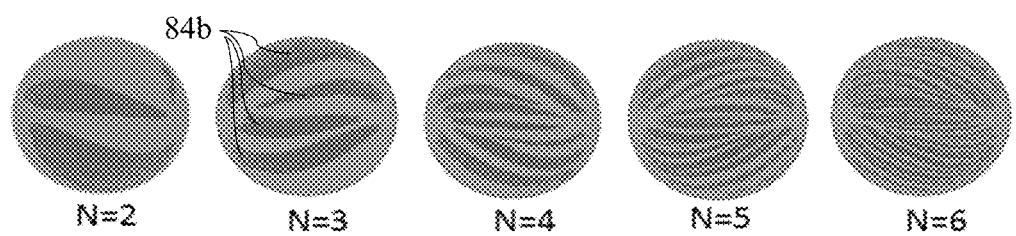
FIG. 6B shows cross sections of material formed by the mixer of FIG. 6A based on the number of helical mixing elements within the static mixer.

To form a multicompartmental filament with an intercalated linear (e.g., striated) structure, as shown in FIG. 6B, varying mixing modules with varying internal geometries can be implemented. For the printing of high-viscosity materials at high flow rates, a mixer with a designed number of internal helical elements can be used. Optionally, the mixer can comprise or be adapted from a KINEX mixer made by Chemineer of Dayton, OH Each internal helical element divides the streams of different materials into two streams, rotates the streams and interfaces them together in reverse order. Therefore, an elongated array of different material chambers is created in the cross-section of the stream, forming a multicompartmental precursor stream. The number of the compartments (x) and their size can be controlled by the number of the implemented helical elements (y) with $x=2^y$. Thus, a mixer 34 with a particular number of helical elements can be coupled to the housing to form the desired number of compartments (e.g., linear compartments 84*b*). In embodiments in which the viscosity of at least one material or the printing rate is low, to generate an intercalated linear structure, the mixer can comprise, instead of helical elements that divide flow evenly, one more elements that split the flow into two streams with different cross sectional areas and interfacing the two streams in the reverse order.

Figure 6C:
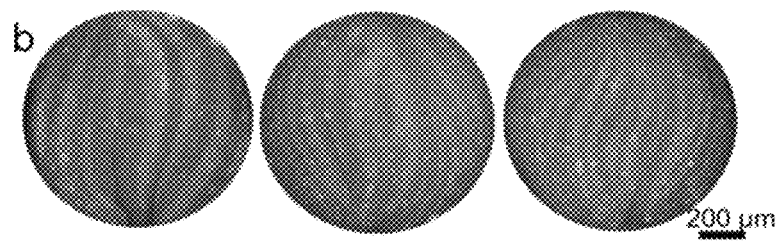
FIG. 6C is an optical microscope view of the cross section of multi-material alginate (pink phase) and GelMA (blue phase) fibers whose cross sections were predicted as in FIG. 6B.
Figure 8A:
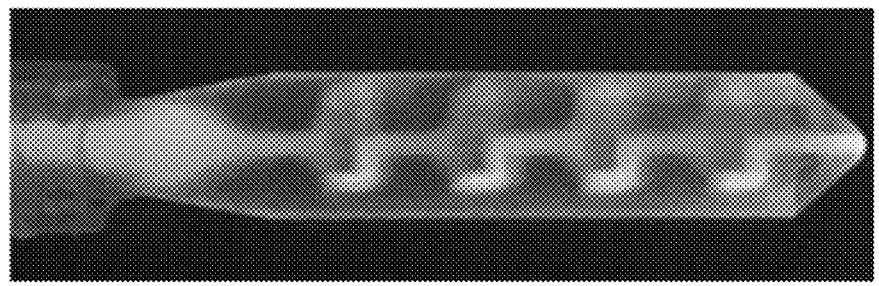
FIG. 8A is an actual view of an exemplary static mixer as disclosed herein.
Figure 8B:
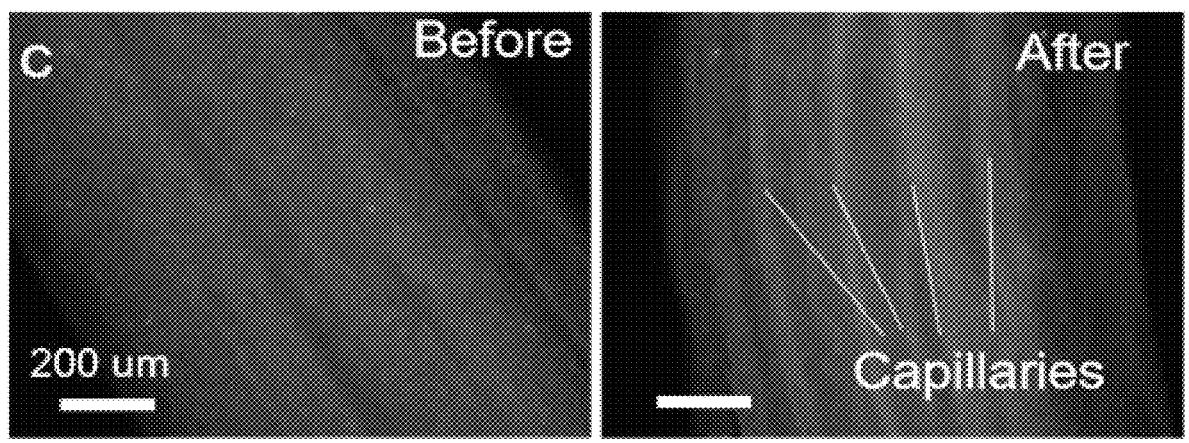
FIG. 8B are actual optical microscope images of side views of exemplary fibers printed using the static mixer from FIG. 8A before and after gelatin has been dissolved (or otherwise removed) to form capillaries.
Figure 8C:
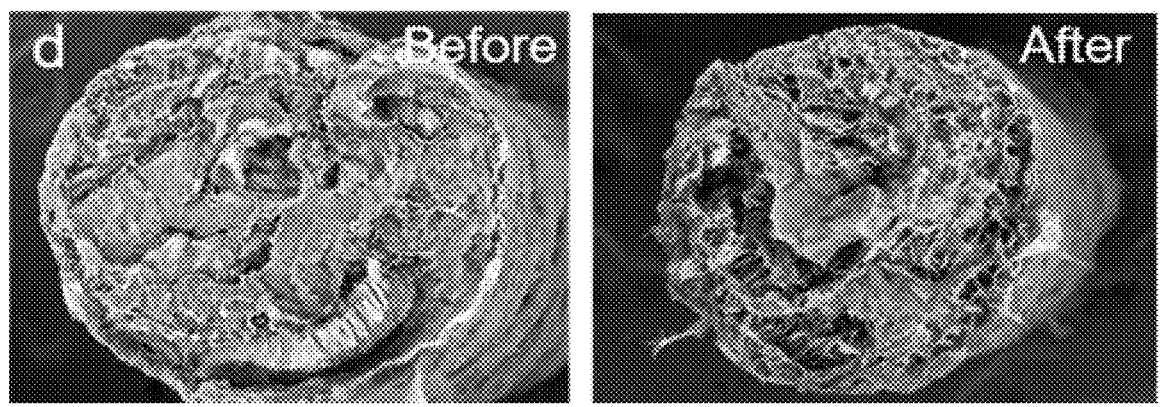
FIG. 8C illustrates scanning electron microscope end views of the fiber before and after the dissolution (or other removal) of the gelatin.

FIGS. 8A-8C illustrate the formation of capillaries in a fiber (filament) using the disclosed printer after incubation of the fibers for 30 min at 37° C. FIG. 6C illustrates different cross-sections of exemplary fibers where GelMA and gelatin are differently colored. FIG. 8B illustrates images before and after gelatin has been dissolved (or otherwise removed) to form capillaries. FIG. 8C illustrates scanning electron microscope end views of the fiber before and after dissolution (or other removal) of the gelatin.

Referring to FIGS. 10A and 10B, in order to form filaments with single- or multi-encapsulated compartments, the mixer 34 can comprise a first channel 80 that flows a first material therethrough and a respective outlet 82 of the second material (and additional materials) within the first channel for each encapsulated compartment positioned within the first flow channel. The outlet(s) can be circular for forming circular compartments 84*a*. Optionally, a plurality of mixers can be placed in series to increase the number of internal compartments. To form coaxial filaments with different internal geometry (FIG. 4B), a specific fluidic system can be implemented with coaxial channels in which the outlet(s) 82 have the desired shape while the external channel has the cross-sectional shape of the nozzle outlet (e.g., circular).

Figure 9A:
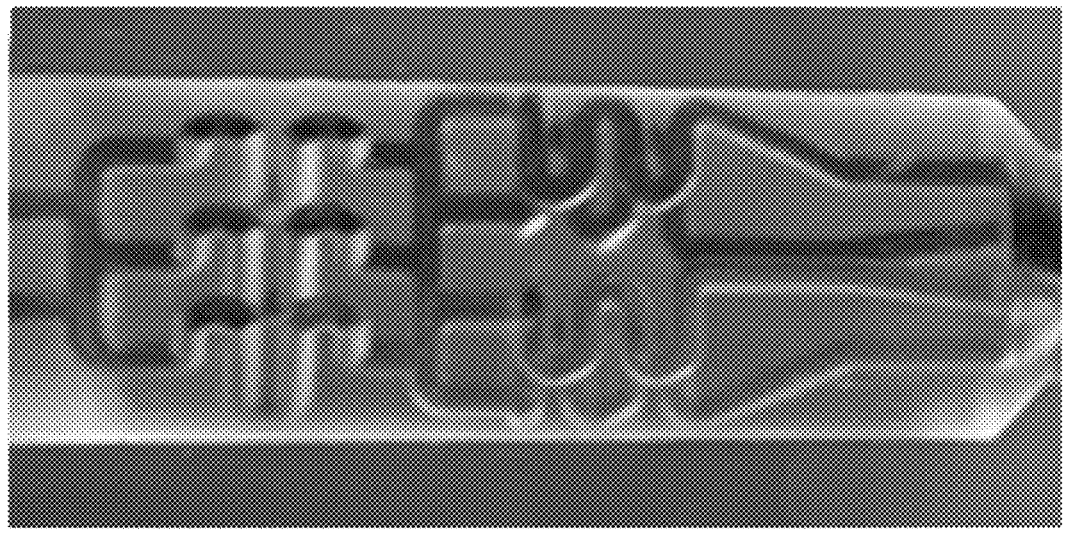
FIG. 9A illustrates a Christmas-tree gradient generator-style mixer.
Figure 9B:
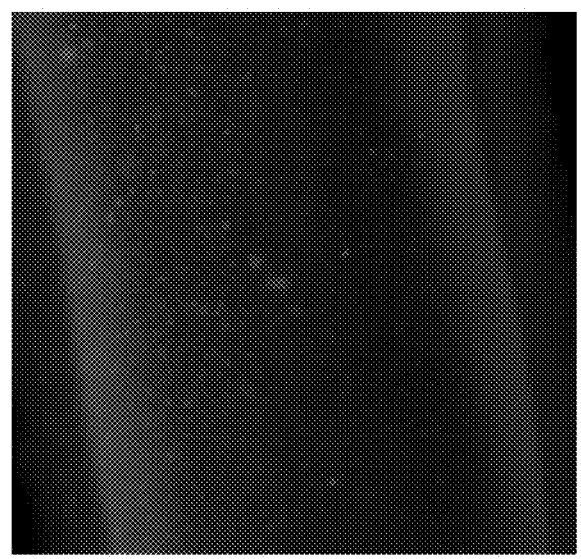
FIG. 9B shows a side view of the filament, demonstrating the ability of the mixer of FIG. 9A to form a continuous gradient of differently colored precursor materials across the cross-section of the extruded fiber.

Referring to FIG. 9A, to form a gradient of materials across the filament (in cross section), a Christmas-tree gradient generator can be used. For example, in some aspects, the streams of different materials are split into two streams, and one stream from each material is interfaced and thoroughly mixed, while another of each material stream is kept unmixed to form minimum and maximum concentrations. The streams can then be combined side-by side. Division and recombination can be repeated in different stages of the Christmas-tree design to form a smooth gradient across the filament. FIG. 9B shows a side view of the filament, demonstrating the ability of the microfluidic mixing chamber to form a continuous gradient of differently colored precursor materials across the cross-section of the extruded fiber. FIG. 9C illustrates pixel intensity quantification across the length of the fiber to demonstrate the continuous gradient.

Method of Use

First and second or more biomaterials can be extruded from the first and second or more containers. The mixer can mix the first and second or more biomaterials to form a mixture having a predetermined cross sectional structure. The mixture can be deposited through the nozzle to form a filament.

After the deposition of the filament, the filament can be crosslinked. The crosslinking can be performed via known physical, thermal, chemical, ionic, and/or enzymatic methods, or combinations thereof. For example, the radiation source 50 can crosslink materials of the deposited filaments using one or more wavelengths of light. In further aspects, crosslinking can be provided by external sources or internal material interactions. For example, a first biomaterial can act as a source of ions to crosslink a second biomaterial through diffusion. The printer can control the degree of crosslinking in the interaction with precursor materials. Further, this printer can use sacrificial (noncrosslinked materials) that can be removed to generate unique architectures and features in the extruded filaments. This can be used to generate vasculature and topographical cues for certain biological applications. For example, gelatin can be printed as circular coaxial compartments within a GelMA outer structure whereby the gelatin can be sacrificed after the GelMA outer structure is crosslinked. In this case, gelatin can melt and/or dissolve (or be otherwise removed) to create microlumens.

Optionally, the nozzle 40 can be positioned in a support bath or other environmental conditions like vapor within the wound in situ to aid physical support, structural complexity, crosslinking, or some other feature of the extrusion process.

The filament or filament subunit can be deposited into a tiddue defect having any dimension and depth. In some aspects, the tissue defect can have an irregular shape and can involve multiple tissues.

EXAMPLES

The multi-material handheld printer 10 can be configured to move multiple precursor materials therethrough. The multi-material handheld printer 10 can further be configured to mix the precursor materials to provide a particular ratio, gradient, or cross sectional structure and then to extrude the mixed precursor materials from the multi-material handheld printer. In this way, the multi-material handheld printer 10 can be used in situ to construct or reconstruct a desired architecture or scaffold, and crosslink extruded material to the tissue of a patient.

Figure 2A:
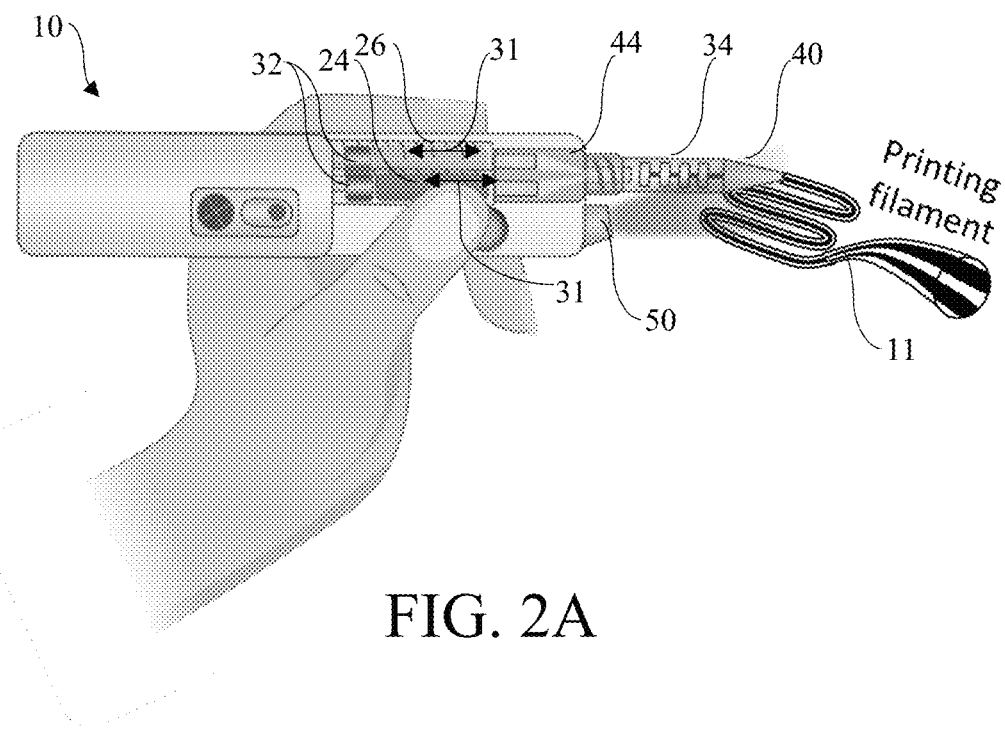
FIG. 2A illustrates an exemplary handheld multi-material bioprinter printing a filament as disclosed herein.
Figure 3:
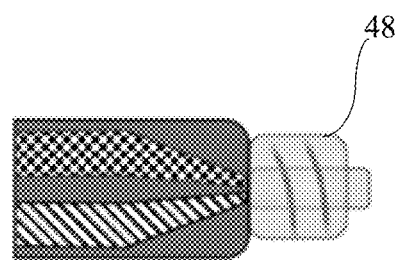
FIG. 3 illustrates a front portion of the printer of FIG. 2 that defines a Luer lock coupling.

In situ printing can eliminate any treatment delays and solves the challenge of implantation of hydrogel-based scaffolds. Furthermore, in situ printing can facilitate the creation of customizable scaffolds which can precisely fill in varied defects. Embodiments disclosed herein can print photocrosslinkable hydrogels, such as gelatin methacryloyl (GelMA), in situ at the time of injury (or shortly thereafter). The handheld printer can have an electric actuator for the delivery of bioink at a controlled constant or varied rate. The printer can have an FDA-approved light source used in dentistry (wavelength of ~420 nm) that can crosslink GelMA in situ (FIG. 2*a*). The printer can allow the use of a lure-lock sterile syringe for loading the GelMA prepolymer. Once GelMA is loaded, the printing speed can be adjusted to facilitate the creation of scaffolds of various sizes and shapes, with uniform filament sizes between 250 to 1000 nm. Lithium phenyl-2,4,6-trimethylbenzoylphosphinate (LAP) can be utilized as the photoinitiator (PI), which can enable the crosslinking of GelMA-based scaffolds within less than 10 seconds of exposure.

Figure 2B:
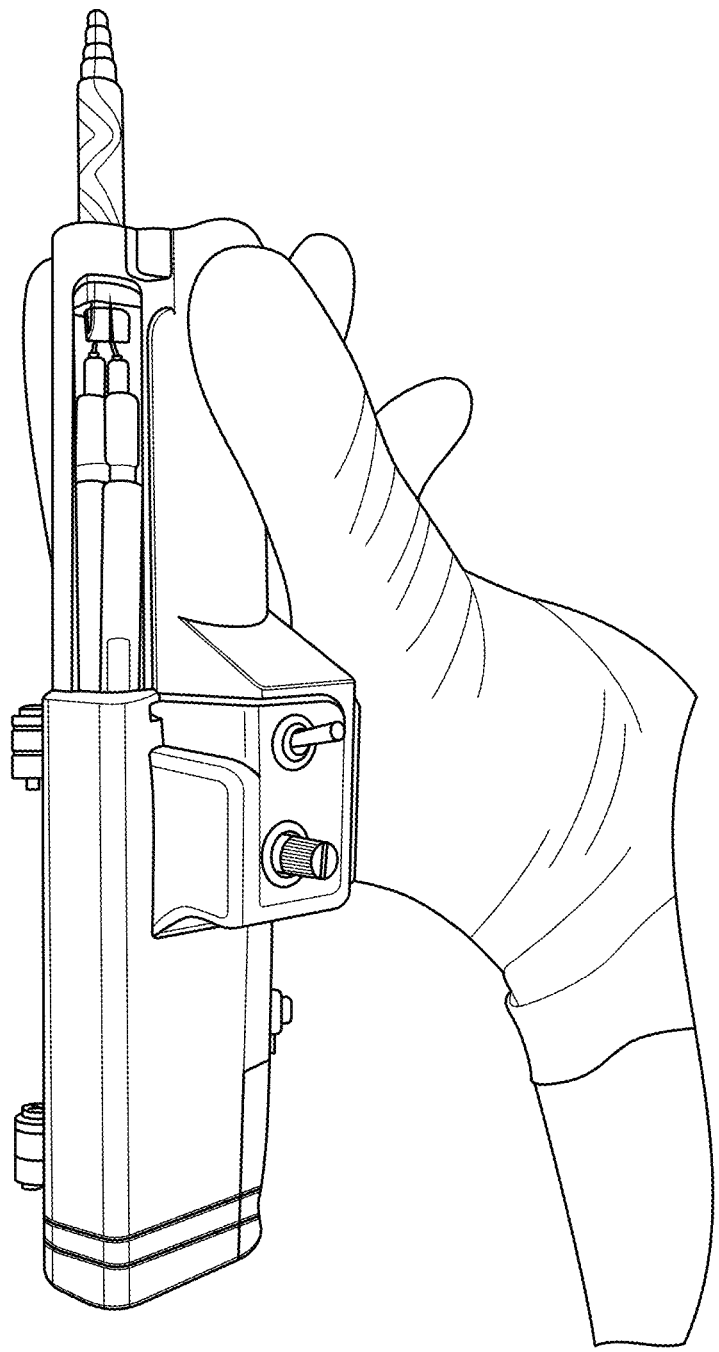
FIG. 2B is an image of an exemplary handheld multi-material bioprinter.
Figure 4A:
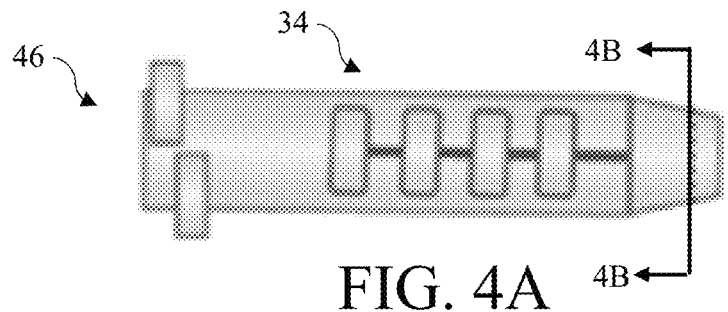
FIG. 4A is a schematic diagram of a mixer of the bioprinter of FIG. 2.
Figure 4B:
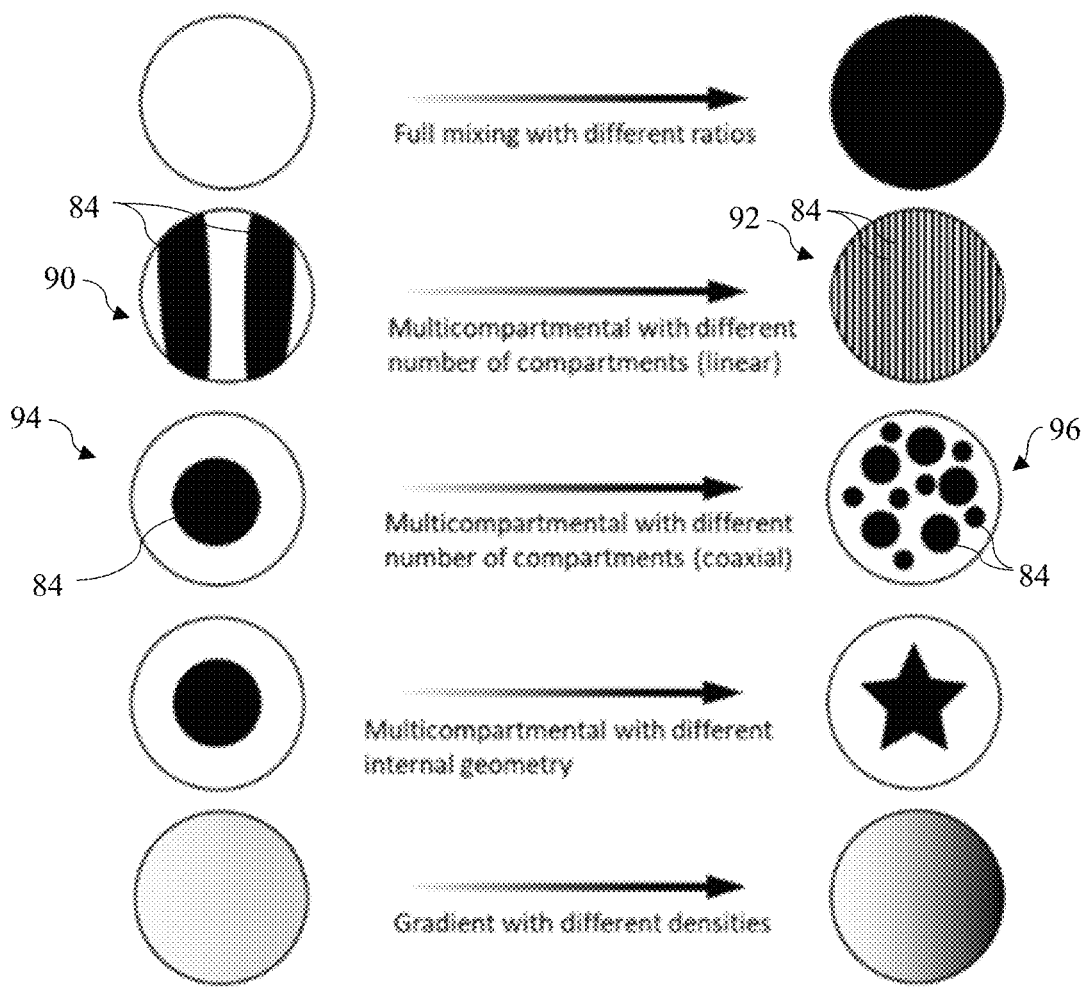
FIG. 4B shows cross sections of different material arrangements formed by the mixer in the plane 4B of FIG. 4A.
Figure 5A:
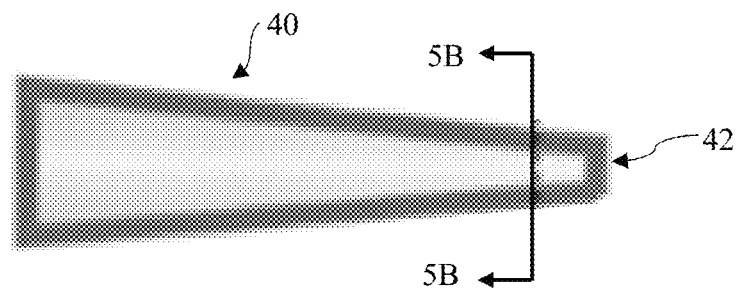
FIG. 5A is a schematic diagram of a nozzle of the bioprinter of FIG. 2.
Figure 5B:
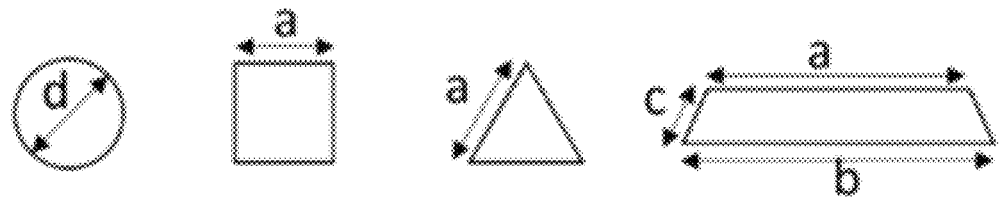
FIG. 5B shows different exemplary cross sections of the nozzle in the plane 5B of FIG. 5A.

In one embodiment, a handheld printer can accommodate two syringes carrying two bioinks. FIG. 2B shows an exemplary multi-material handheld printer.

The developed multi-material handheld printer can address the requirements previously described for tissue regeneration. Particularly, four main requirements were tested: (A) formation of high cell-scale features within each filament for guiding cellular organization; (B) formation of capillaries (e.g., microcapillaries) to improve nutrition transfer and help vascularization of the scaffold; (C) formation of a gradient across a single fiber for printing scaffolds at the interface of two different tissues; (D) formation of a strong adhesion upon in situ crosslinking to resolve the challenge of scaffold fixation upon implantation.

The physiological process of angiogenesis within thick and large-sized implants is time-consuming, which results in the failure of clinically sized implants due to massive starvation-induced cell death within the implant. Three-dimensional (3D) scaffolds that incorporate hollow microchannels have shown faster angiogenesis in vivo due to the microchannels, which induced the rapid recruitment of satellite cells into the implants.

Figure 6D:
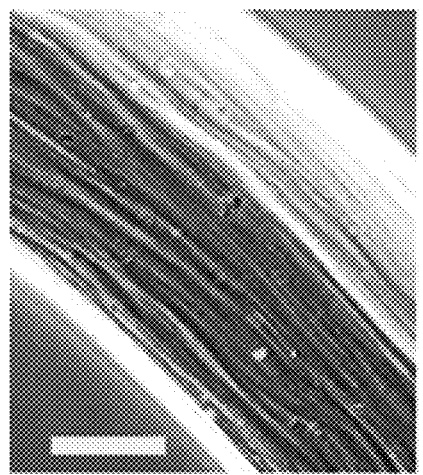
FIG. 6D is an optical microscope view of a side profile view of a multi-material alginate/GelMA fiber, showing microfilaments of GelMA formed in the alginate fiber.
Figure 6E:
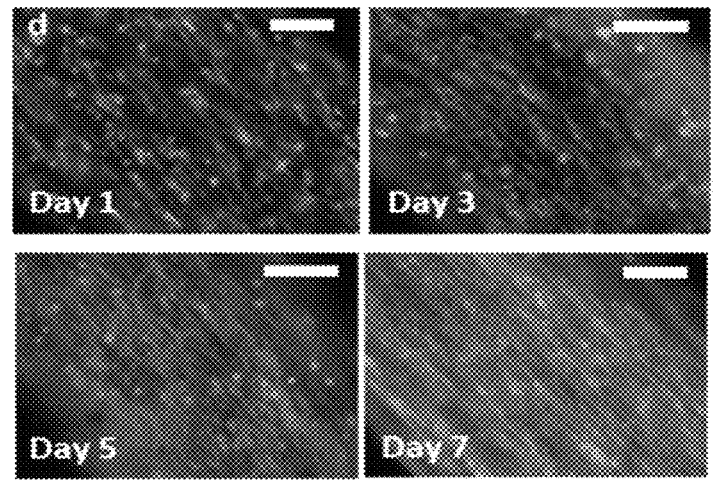
FIG. 6E shows proliferation of cells in the hydrogel fiber of FIG. 6D and formation of multinucleated myofibers after 7 days in differentiation.
Figure 6F:
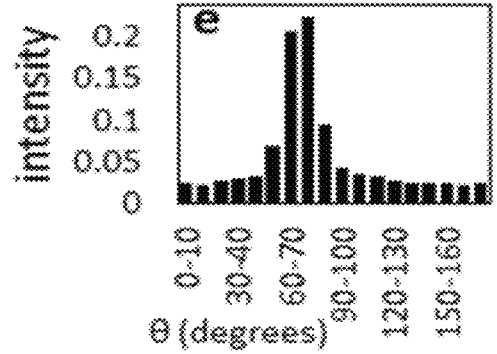
FIG. 6F illustrates the orientation of cells after 1 day of culture.
Figure 6G:
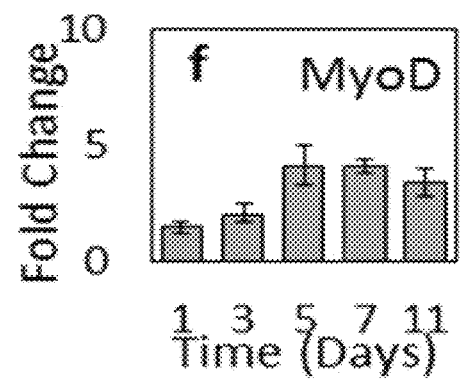
FIGS. 6G, 6H, and 6I show expression of early and late respective myogenic markers indicating the myogenesis inside the multi-material fibrillar hydrogel.
Figure 6H:
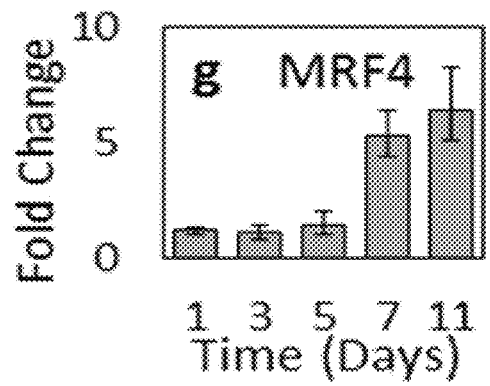
Figure 6I:
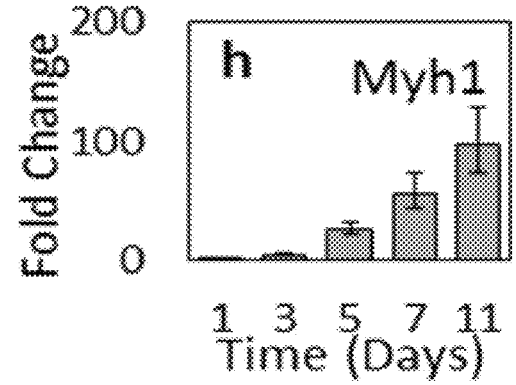

Formation of multi-material hydrogel fibers with intrinsic microfilaments can direct cellular organization. As shown in FIG. 6A, a static mixer (e.g., a 3D-printed static mixer) with a coaxial microfluidic device can be used to create fibers (e.g., meter-long fibers) (FIG. 6C) that embed sequential filaments of various hydrogels including alginate and GelMA. The thickness of the fiber can be controlled by changing the core-to-sheath flowrate ratio while the size of internal filaments is manipulated from millimeter to micrometer scales through changing the number of distributor elements (e.g., helical mixing elements). For example, as shown in FIG. 6B, depending on the number of helical mixing elements, different numbers of internal filaments can be formed. The results demonstrate that the biofabrication strategy disclosed herein not only supports high cellular viability, but also can induce the filament alignment, which is ideal for muscle-tissue engineering. By optimizing the number of distributor elements, a range of microfilaments sizes was discovered. FIG. 6D illustrates the proliferation of cells in hydrogel fiber and formation of multinucleated myofibers after 7 days in differentiation. FIG. 6E illustrates the orientation of cells after 1 day of culture. The biomimetic structure of the fibers with a high level of fibrillar organization can accelerate the formation of fascicle-like structures. Using gene expression analysis, it was confirmed that the developed fibrillar scaffold supported cellular differentiation, as indicated by the charts in FIGS. 6F-7H.

Figure 11D:
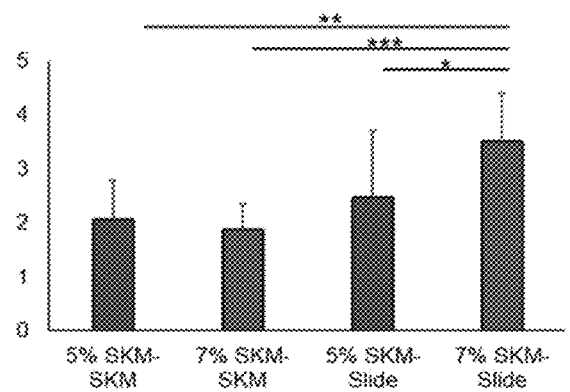
FIG. 11D shows test results of adhesion stress of scaffolds against shear forces.
Figure 12A:
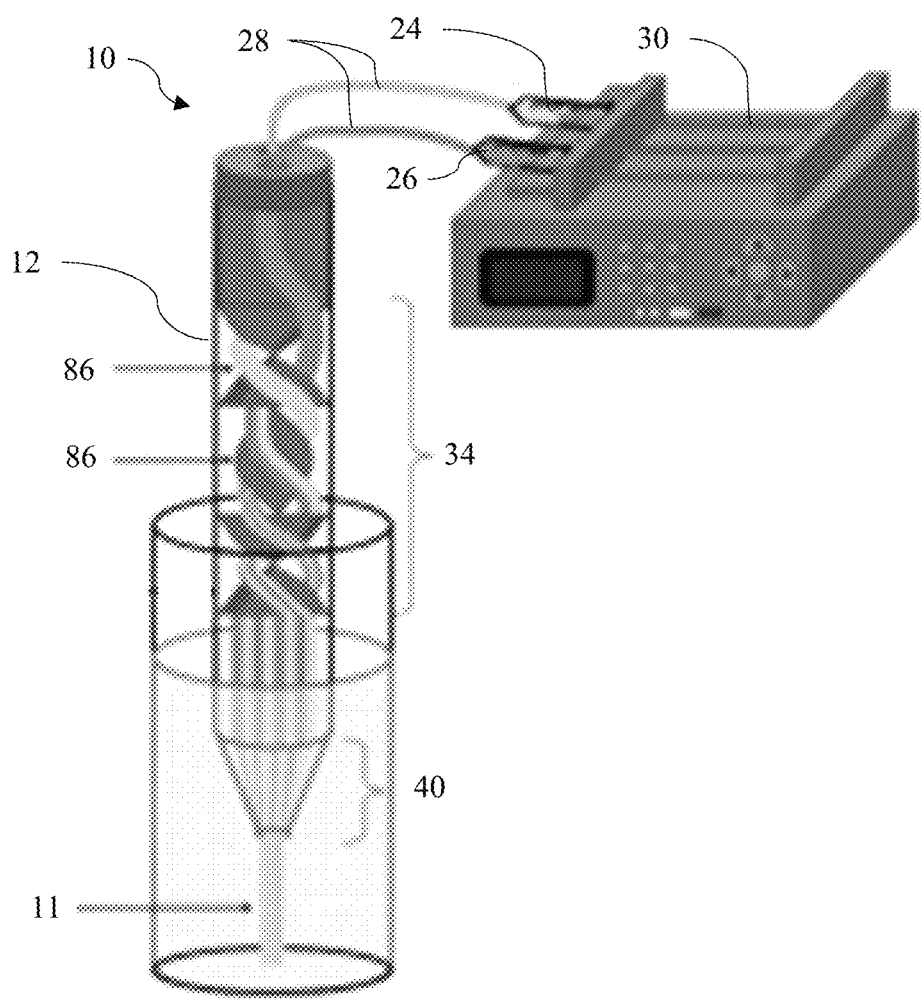
FIG. 12A is a perspective view of an exemplary bioprinter as disclosed herein.
Figure 12B:
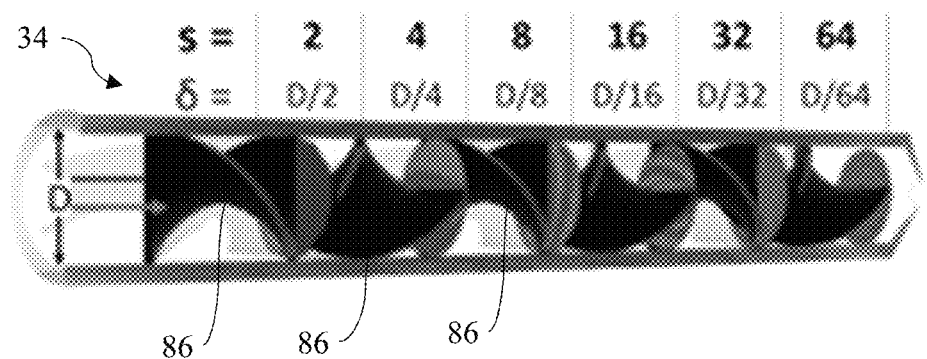
FIG. 12B is a sectional view of an exemplary static mixer as disclosed herein, showing a plurality of helical mixing elements.
Figure 12C:
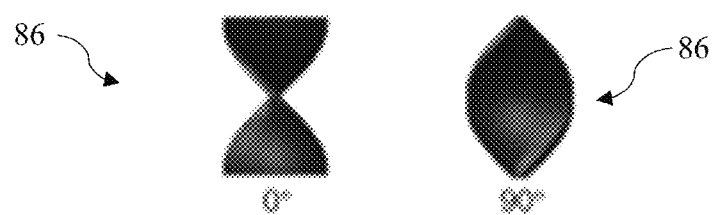
FIG. 12C depicts views at 0 and 90 degree side angles of one helical mixing element of FIG. 12B.

Referring to FIGS. 11A-11D, adhesion of exemplary scaffolds to native tissues upon in situ printing was assessed. Shear and tensile ultimate adhesion strength increased as GelMA concentration increases from 5% (w/v) to 7% (w/v). The values are within the range of mechanical loads recorded in skeletal muscle of animal models. The shear adhesion strength was measured by printing and crosslinking of GelMA hydrogels between substrates of two varying conditions: skeletal muscle adhered to glass slides on both sides (SKM-SKM), as well as muscle adhered to a glass slide on one side and glass slide on the other (SKM-Slide). The first condition was representing the corners of the defect site in which scaffolds are confined by the surrounding tissue, and the latter case represented the middle section where the scaffold has one interface with the host tissues. A similar exemplary test has verified the scaffold adhesion to pig skin. FIG. 11A shows an exemplary structure of in situ printed GelMA undergoing tensile forces, and FIG. 11B shows test results of adhesion stress. FIG. 11C shows an exemplary structure of in situ printed GelMA undergoing shear forces, and FIG. 11D shows test results of adhesion stress of scaffolds against shear forces.

The multi-material handheld bioprinter can be configured to print photocrosslinkable hydrogels, such as gelatin methacryloyl (GelMA), in situ at the time of injury (or shortly thereafter). In situ printing can eliminate any treatment delays and solve the challenge of implantation of hydrogel-based scaffolds (FIG. 1). Furthermore, in situ printing facilitates the creation of customizable scaffolds that can precisely fill in varied muscle defects. However, there are two important challenges that can affect the formation of functional and aligned contractile myotubes: 1) lack of topographical cues in hydrogel fiber with dimeters larger than 500 μm; and 2) diffusion limit of nutrients and oxygen in such fibers. The survival of implanted cell-laden scaffolds can be dependent on oxygenation by its connection to the blood circulation of the host body. The physiological process of angiogenesis within thick and large sized implants is time-consuming, which results in the failure of clinically sized implants due to massive starvation-induced cell death within the implant. Hollow microchannel incorporated three-dimensional (3D) scaffolds have shown faster angiogenesis in vivo due to the microchannels, which induced the rapid recruitment of satellite cells into the implants. Embodiments disclosed herein can overcome these challenges. It is contemplated that scaffolds can be printed using a handheld bioprinter that deposits filaments having internal capillaries (e.g., microcapillaries).

Figure 7A:
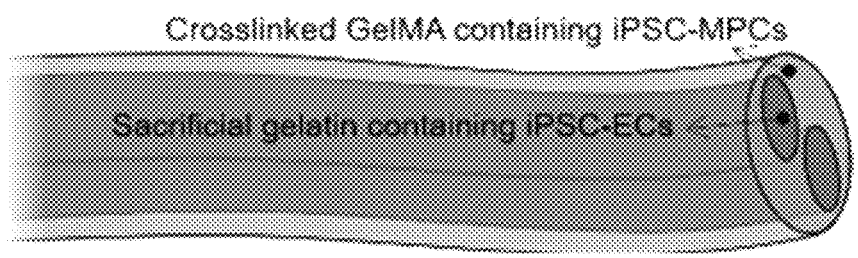
FIG. 7A illustrates an example of a multi-material filament that is composed of a sacrificial gelatin core and GelMA outer structure printed by the handheld bioprinter.
Figure 7B:
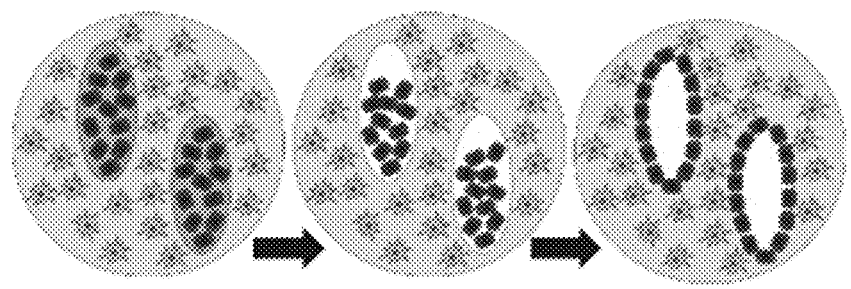
FIG. 7B illustrates the cross sections of the printed filament from FIG. 7A forming channels therein.

In the formation of multi-material hydrogel fibers with intrinsic microfilaments, a method can include integrating a 3D-printed static mixer (FIG. 4B) with a coaxial microfluidic device to create fibers (optionally, meter-long fibers) embedding sequential filaments of various hydrogels including alginate and GelMA (FIG. 7A). The thickness of the fiber can be controlled by changing the core-to-sheath flowrate ratio while the size of internal filaments can be manipulated from millimeter to micrometer scales through changing the number of mixing elements (FIG. 6B). The results demonstrate that the biofabrication strategy not only supports high cellular viability, but also can induce their alignment, ideal for muscle-tissue engineering. By optimizing the number of distributor elements, a range of microfilaments sizes can be formed. The biomimetic structure of the fibers with a high level of fibrillar organization can accelerate the formation of fascicle-like structures. Using gene expression analysis, it was confirmed that the developed fibrillar scaffold supported cellular differentiation.

In various optional aspects, the printer can be used to form vascularized tissues.

In some optional aspects, the printer can be coupled to a robotic arm or manual surgeon-guided mechanical device. It is contemplated that the robotic arm can enhance the resolution or accessibility to the wound of the printing.

The mixer can repeatedly split/reorient materials as they flow through each element (a print head containing 1, 2, 3, 4, 5, or 6 elements will then create 2, 4, 8, 16, 32, or 64 striations, respectively). Multi-lamellar structures can be printed using a single nozzle by co-extruding two different materials through a static mixer (e.g., one or more helical static mixer elements). Potential for high resolution can be achieved. The resolution, namely the number of lamellae and the distance between them (6), can be tuned using different numbers of helical static mixer elements. Results suggest alignment of the microstructures within the fibers resulted in a more reproducible mechanical performance in structurally complex materials such as alginate hydrogels.

In some aspects, different hydrogels or multi-compartment hydrogels with sacrificial components can be mixed with the mixer.

Solid filaments of gel can be deposited for in situ treatment of musculoskeletal and skin disorders in patients. Channels and capillaries can be formed during printing.

Advantages

Advantages of one or more embodiments of the disclosed handheld multi-material bioprinter can include:

The ability to print multiple materials from a single handheld printer (optionally, simultaneously);

The formation of filaments with the controlled spatial pattern of different compartments with cell-scale resolution;

Fabrication of scaffolds in which every single filament creates a biomimetic microenvironment with embedded capillaries (e.g., microcapillaries) and designed physical and chemical properties;

Spatial control of the multiple materials interaction within a filament;

Printing different internal compartments with adjustable size, architecture, and level of mixing; and Printing such constructs with a portable device diversifies the potential applications of the printer.

Printing such constructs with a spatially controlled device that is manually operated by the surgeon/technician removes the need for expensive imaging, drafting, modeling, and computing hardware, software, and technical expertise. Still further, the printer can allow manual control of the spatial deposition without the use of a coordinate system.

Exemplary Uses

The disclosed multi-material handheld bioprinter can be used in research and teaching institutions and can have further medical applications ranging from the treatment of tissue defects including but not limited to skin injuries, reconstruction of cancer dissection sites, treatment of muscle injuries, bone loss, and cardiac defects.

For research institutions, exemplary users of the disclosed multi-material handheld bioprinter can include academic researchers (pre-doctoral researchers, post-doctoral researchers, principal investigators, etc.). The multi-material handheld bioprinter can have applications in biomaterial testing, additive manufacturing, and biomedical research (in vitro, in vivo studies). The applications can include any potential use where a controlled deposition of liquid materials is useful.

For teaching institutions, exemplary users of the disclosed multi-material handheld bioprinter can include students in laboratory-based courses, lecturing professors, and scientific outreach activists. These individuals can use the device for the additive construction of precursor materials as demonstrations of key educational concepts. The handheld printer can require lower infrastructure than computer-controlled, stationary devices. The lower infrastructure cost can increase their use for demonstrative and educational purposes.

For medical applications, exemplary users of the disclosed multi-material handheld bioprinter can include procedural, wound prep, and wound management care providers. The medical applications can range from public hospitals, private practices, and military health care. The end user can include field medics, paramedics, dermatologists, plastic surgeons, wound care nurses, orthopedic surgeons, cardiothoracic surgeons, etc. The ability to have facile control over the composition and organization of subfeatures within a printed scaffold can increases the number of applications over single-material printing; this increase in versatility has direct applications in tissue interfaces, tissue bonding, tissue regeneration, and tissue reconstruction.

Computing Device

Figure 13:
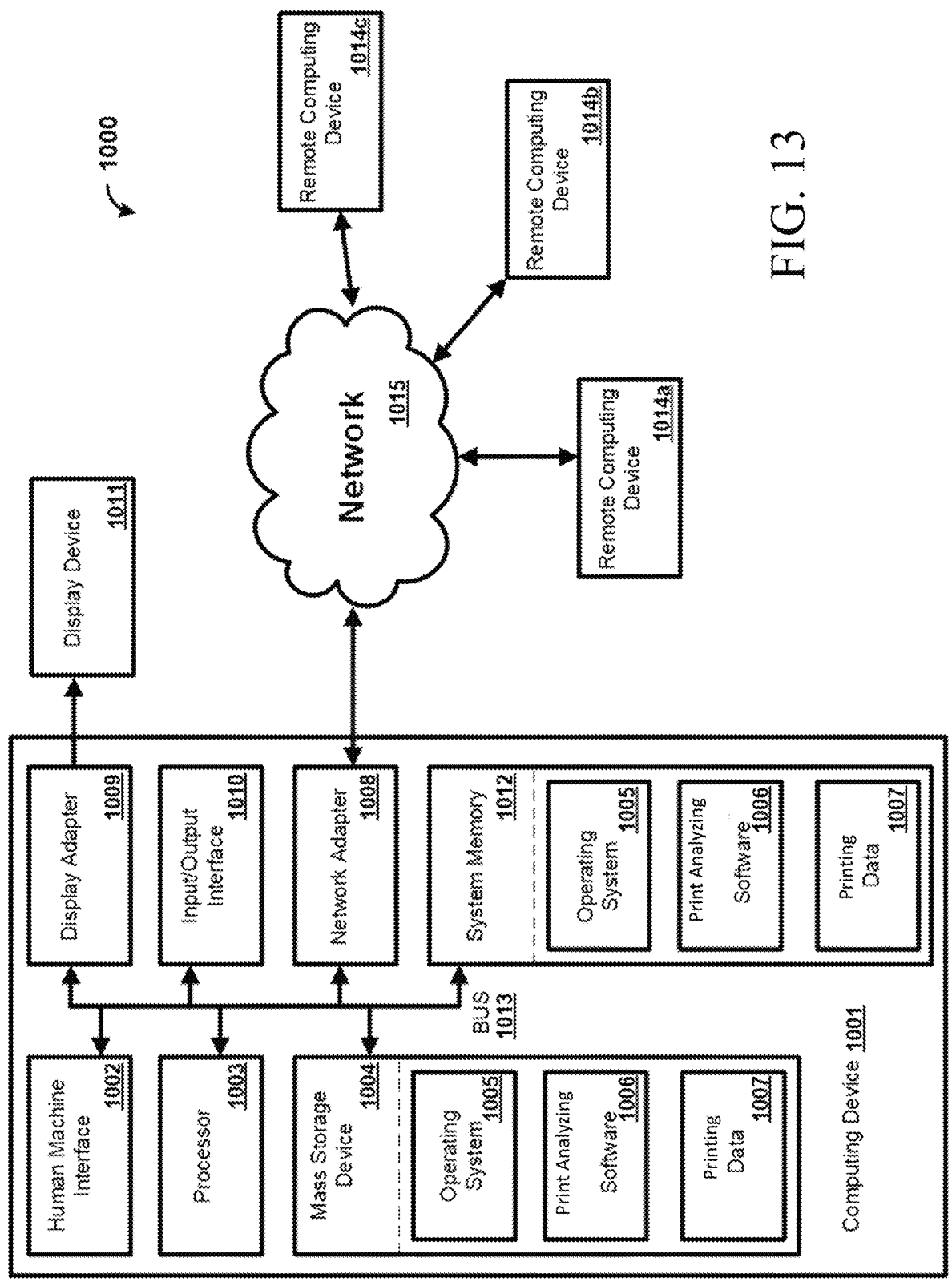
FIG. 13 shows an operating environment including an exemplary configuration of the computing device that can be used with the exemplary bioprinter as disclosed herein.

FIG. 13 shows an operating environment 1000 including an exemplary configuration of the computing device 1001 that can be used with the printer 10. Further, elements of the computing device can be integral to the printer 10. Still further, elements of the printer 10, such as, for example, the microcontroller 56 (FIG. 6), can be configured as disclosed herein with reference to the computing device 1001. The computing device 1001 may comprise one or more processors 1003, a system memory 1012, and a bus 1013 that couples various components of the computing device 1001, including the one or more processors 1003, to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as printing data 1007 and/or program modules such as operating system 1005 and orientation calculating software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and print analyzing software 1006 may be stored on the mass storage device 1004. One or more of the operating system 1005 and print analyzing software 1006 (or some combination thereof) may comprise program modules and the print analyzing software 1006. The printing data 1007 may also be stored on the mass storage device 1004. The printing data 1007 may be stored in any of one or more databases known in the art. The databases may be centralized or distributed across multiple locations within the network 1015.

A user may enter commands and information into the computing device 1001 using an input device (not shown). Such input devices comprise, but are not limited to, a keyboard, pointing device (e.g., a computer mouse, remote control), a microphone, a joystick, a scanner, a touchscreen, tactile input devices such as gloves, and other body coverings, motion sensor, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014*a,b,c*. A remote computing device 1014*a,b,c* may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014*a,b,c* may be made using a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014*a,b,c* can optionally have some or all of the components disclosed as being part of computing device 1001. In further optional aspects, the remote computing device 1014*b* can be a server that receives and stores logged data from the printer. In optional aspects, some or all data processing can be performed via cloud computing on a computing device or system that is remote to the computing device 1001.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of print analyzing software 1006 may be stored on or sent across some form of computer readable media. Any of the disclosed methods may be performed by processor-executable instructions embodied on computer readable media.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A multi-material printer comprising:
a housing that is configured to be handheld, wherein the housing is configured to receive first, second, and/or additional printable materials from respective first, second, and/or additional containers;
a nozzle in communication with the housing, wherein the nozzle defines an outlet of the multi-material printer; and
at least one actuator that is configured to cause the first, second, and/or additional printable materials from the first, second, and/or subsequent containers to flow through the housing at a respective controlled constant rate,
wherein the multi-material printer is configured to simultaneously extrude the first, second, and/or additional printable materials from the outlet.

Aspect 2: The multi-material printer of aspect 1, further comprising the first, second, and/or additional containers, each having the respective first, second, and/or additional printable materials therein, wherein at least one of the first, second, and/or additional printable material comprises a biomaterial.

Aspect 3: The multi-material printer of aspect 2, wherein the multi-material printer is capable of extruding, mixing, and crosslinking materials of varying chemical, structural, and physical properties that can be mixtures of materials, cells, growth factors, nucleic acids, lipids, and other biomaterials.

Aspect 4: The multi-material printer of aspect 2, wherein one or more of the first, second, and/or additional printable materials are configured to be removed from the extruded filament or subfilament to form cavities.

Aspect 5: The multi-material printer of aspect 2, wherein the biomaterials can interact to crosslink, form secondary structures, foam, gas, cause destructive or constructive interference, etc.

Aspect 6: The multi-material printer of aspect 2, wherein the first, second, and/or additional containers are coupled to the housing by a flexible conduit.

Aspect 7: The multi-material printer of aspect 2, wherein the first, second, and/or additional containers configured to be received at least partially within the housing or secondary storage device.

Aspect 8: The multi-material printer of aspect 1, wherein the first, second, and/or subsequent containers are configured to be received within the housing, wherein each of the first, second, and/or subsequent containers comprises:
a longitudinal axis; and
a plunger with a moveable component along the longitudinal axis,
wherein the at least one actuator is configured to move the plunger of each container along the respective longitudinal axis of the container at a controlled constant or varied rate.

Aspect 9: The multi-material printer of aspect 1, further comprising a mixer that is configured to mix the respective first, second, and/or subsequent materials from the first, second, and/or additional containers Aspect 10: The multi-material printer of aspect 9, wherein the mixer comprises at least one mixing element that can generate lengthwise or cross sectional features including different mixing ratios, linear compartments, coaxial compartments, multicompartmental geometries, gradients, or any combination of the aforementioned conditions of different biomaterials.

Aspect 11: The multi-material printer of aspect 10, wherein at least one helical mixing element comprises a plurality of helical mixing elements that are longitudinally spaced along the mixer, wherein adjacent mixing elements of the plurality of mixing elements are rotationally offset from each other.

Aspect 12: The multi-material printer of aspect 9, wherein the bioprinter is configured to print a filament or subunit of a larger tissue construct such as a drop comprising a plurality of linear or radial compartments.

Aspect 13: The multi-material printer of aspect 9, wherein the mixer is a Christmas-tree gradient generator-style mixer.

Aspect 14: The multi-material printer of aspect 9, wherein the mixer and nozzle are unitarily formed as a monolithic component.

Aspect 15: The multi-material printer of aspect 9, wherein the mixer and nozzle is configured to print internal sub-filament structures for the creation of vasculature, nerves, or lymphatic systems.

Aspect 16: The multi-material printer of aspect 1, further comprising one or more radiation sources that are configured to emit various wavelengths and intensities of radiation for crosslinking hydrogel and biomaterials at any point in the extrusion process.

Aspect 17: The multi-material printer of aspect 1, further comprising of one or more sources that are configured to emit various wavelengths and intensities of sound for manipulating the biomaterial or its constituents at any point of the extrusion process.

Aspect 18: The multi-material printer of aspect 1, further comprising of a source that is configured to emit chemical, ionic, physical, or enzymatic agents at any point of the extrusion process to aid in disinfection, crosslinking, generation of internal or external geometries, or other features.

Aspect 19: The multi-material printer of aspect 1, further comprising of a source that is configured to heat the air around the extruded filament or subunit at the point of extrusion process to aid in crosslinking, reduction in contamination, removal of temperature-sensitive materials, etc.

Aspect 20: The multi-material printer of aspect 1, where the nozzle can be printed in a support bath or other environmental conditions like vapor within the wound in situ to aid physical support, structural complexity, crosslinking, or some other feature of the extrusion process.

Aspect 21: The multi-material printer of aspect 1, wherein the first container comprises a first plunger and the second and/or subsequent container comprises a second and/or subsequent plungers, wherein the at least one actuator comprises a first actuator that is configured to actuate the plunger of the first container and a second and/or subsequent actuators that are configured to actuate the plunger of the second and/or subsequent containers via direct contact, pneumatic, screw, or other physical means.

Aspect 22: The multi-material printer of aspect 21, wherein the first, second, and/or subsequent actuators are independently controllable to cause the plungers of the at least two syringes to move at different linear or varying rates.

Aspect 23: The multi-material printer of aspect 1, where the nozzle has any geometric shape and array of shapes.

Aspect 24: A method comprising:
extruding, from first, second, and/or subsequent containers, first, second, and/or additional biomaterials;
mixing, with a mixer, the first, second, and/or additional biomaterials to form a mixture having a predetermined cross sectional structure and composition;
depositing, through a nozzle, the mixture to form a filament or subunit such as a drop; and
where the nozzle or deposition of the extruded material is controlled manually via direct or indirect means.

Aspect 25: The method of aspect 24, wherein depositing the mixture to form the filament or subunit of a scaffold comprises depositing the mixture for treating a defect or injury in musculoskeletal, skin, bone, eye, mucosal, heart, liver tissues, or reconstructing new tissues for cosmetic or non-cosmetic purposes in a subject in need thereof, comprising: using a handheld printer to directly deposit printing materials on or into the defect of the subject (patient, animal, etc).

Aspect 26: The method of aspect 24, wherein the predetermined cross sectional structure comprises linear or radial striations of the first, second, and/or subsequent materials.

Aspect 27: The method of aspect 26, wherein the mixer generates different cross sectional mixing ratios, linear compartments, coaxial compartments, multicompartmental geometries, gradients, etc. of the biomaterials.

Aspect 28: The method of aspect 24, wherein the biomaterials are extruded from actuators via direct contact, pneumatic, screw, or other physical means.

Aspect 29: The method of aspect 28, wherein the extrusion of each biomaterial can be controlled individually or simultaneously at constant or varying rates.

Aspect 30: The method of aspect 24, wherein the printing materials comprises at least one of a polymer, a protein, nucleic acids, lipids, ceramic, mixture, or other biomaterials wherein printing material comprises any polymer such as polycaprolactone, polylactic acid, poly glucolic acid and their co-polymers, alginate, chitosan, etc, proteins for example collagen or gelatin, etc and their mixtures. The polymers, proteins or their mixtures can be functionalized with different chemicals and chemistries. The polymers or their mixture or proteins and their mixtures can be mixed with nanoparticles of any shape or microparticles of any shape made or chemicals made from any material composition examples are metal (silver, gold, magnesium, zinc, selenium, etc), metal oxides, metal peroxides, bioglasses, radiopaque agents, antibacterial compounds and agents, antimicrobial compounds and agents, antibiotics, bioceramics, ceramics, oxygen generating materials, crosslinking agents, proteins, vitamins, lipids, phospholipids, fatty acids, biological factors, polysaccharides, nucleic acids, growth factors, hydroxyapetite, calcium phosphate, carbon nanotubes, quaternary ammonium compounds, graphene, graphene oxide, carbon derived materials, liquid crystals, peptides, chitosan, silver nitride, platelet rich plasma, bone marrow-derived materials, pain killers, anti-inflammatory drugs or reagents, blood-derived materials and their combinations, etc. The concentrations of the nanoparticles or microparticles or chemicals can be having any range.

Aspect 31: The method of aspect 24, wherein the filament or subunit is deposited into a tissue defect, wherein the tissue defect has any dimension and depth.

Aspect 32: The method of aspect 23, wherein the filament or subunit is deposited into a tissue defect, wherein the tissue defect has an irregular shape and involves multiple tissues.

Aspect 33: The method of aspect 24, wherein the extruded filament comprises two or multiple different cell types, growth factors mixed or placed in distinct regions.

Aspect 34: The method of aspect 33, wherein the extruded filament comprises two or multiple different cell types, growth factors mixed or placed in distinct regions to form vasculatular, neural, or lymphatic systems.

Aspect 35: The method of aspect 24, wherein the extruded filament comprises a sacrificial component to form channels or conduits during or after printing.

Aspect 36: The method of aspect 24, wherein one of the biomaterials is sacrificed to form internal capillaries and structures for the generation of cell-scale cues; construction of other features like vasculature, nerve, or lymph systems; etc.

Aspect 37: The method of aspect 24, wherein a radiation source can emit varying wavelengths of radiation for crosslinking hydrogel at any point in the extrusion process.

Aspect 38: The method of aspect 24, wherein a source that is configured to emit varying wavelengths of sound can manipulate the biomaterial at any point of the extrusion process.

Aspect 39: The method of aspect 24, wherein emitted chemical, ionic, physical, or enzymatic agents at any point of the extrusion process can aid in disinfection, crosslinking, generation of internal or external geometries, or other features.

Aspect 40 The method of aspect 24, wherein a source that is configured to heat the air around the extruded filament or subunit at the point of extrusion process to aid in crosslinking, reduction in contamination, removal of temperature-sensitive materials, etc.

Aspect 41: The method of aspect 24, wherein the nozzle can be printed in a support bath within the wound in situ to aid physical support, structural complexity, crosslinking, or some other feature of the extrusion process.

Aspect 42: A multi-material printer comprising:
a housing that is configured to be handheld, wherein the housing is configured to receive first and second printable materials from respective first and second containers;
a nozzle in communication with the housing, wherein the nozzle defines an outlet of the multi-material printer; and
at least one actuator that is configured to cause the first and second printable materials from the first and second containers to flow through the housing at a respective constant rate,
wherein the multi-material printer is configured to simultaneously extrude the first and second printable materials from the outlet.

Aspect 43: The multi-material printer of aspect 42, further comprising the first and second containers, each having the respective first or second printable materials therein, wherein at least one of the first printable material or the second printable material comprises a biomaterial.

Aspect 44: The multi-material printer of aspect 43, wherein the first and second containers are coupled to the housing by a flexible conduit.

Aspect 45: The multi-material printer of aspect 43, wherein the first and second containers are received at least partially within the housing.

Aspect 46: The multi-material printer of any one of aspects 42, 43, or 45, wherein the first and second containers are configured to be received within the housing, wherein each of the first and second containers comprises:
a longitudinal axis; and
a plunger that is movable along the longitudinal axis, wherein the at least one actuator is configured to move the plunger of each container along the respective longitudinal axis of the container at a constant linear rate.

Aspect 47: The multi-material printer of aspect any one of aspects 42-46, further comprising a mixer that is configured to mix the respective first and second materials from the first and second containers Aspect 48: The multi-material printer of aspect 47, wherein the mixer comprises at least one helical mixing element.

Aspect 49: The multi-material printer of aspect 48, wherein the at least one helical mixing element comprises a plurality of helical mixing elements that are longitudinally spaced along the mixer, wherein adjacent mixing elements of the plurality of mixing elements are rotationally offset from each other.

Aspect 50: The multi-material printer of aspect 47, wherein the bioprinter is configured to print a filament comprising a plurality of linear compartments.

Aspect 51: The multi-material printer of aspect 47, wherein the mixer is a Christmas-tree gradient generator-style mixer.

Aspect 52: The multi-material printer of any one of aspects 47-51, wherein the mixer and nozzle are unitarily formed as a monolithic component.

Aspect 53: The multi-material printer of any one of aspects 42-52, further comprising a radiation source that is configured to emit light for crosslinking hydrogel that has exited the nozzle.

Aspect 54: The multi-material printer of aspect 43, wherein the first container comprises a first plunger and the second container comprises a second plunger, wherein the at least one actuator comprises a first actuator that is configured to actuate the plunger of the first container and a second actuator that is configured to actuate the plunger of the second container.

Aspect 55: The multi-material printer of aspect 54, wherein the first and second actuators are independently controllable to cause the plungers of the at least two syringes to move at different linear rates.

Aspect 56: The multi-material printer of aspect any one of aspects 42-55, further comprising the first and second containers, each having printable material therein, wherein the printable material of at least the first container or the second container comprises a biomaterial.

Aspect 57: The multi-material printer of aspect 56, wherein the first and second containers are coupled to the housing by a flexible conduit.

Aspect 58; The multi-material printer of aspect 56, wherein the first and second containers are received at least partially within the housing.

Aspect 59: A method comprising:
extruding, from first and second containers, first and second biomaterials;
mixing, with a mixer, the first and second biomaterials to form a mixture having a predetermined cross sectional structure; and
depositing, through a nozzle, the mixture to form a filament.

Aspect 60: The method of aspect 59, wherein depositing the mixture to form the filament comprises depositing the mixture on or within a body of a patient.

Aspect 61: The method of aspect 59, wherein the predetermined cross sectional structure comprises linear striations of the first and second materials.

Although the foregoing invention has been described in some detail by way of illustration and example for purposes of clarity of understanding, certain changes and modifications may be practiced within the scope of the appended claims.

What is claimed is:

1. A multi-material printer comprising:
 a housing that is configured to be handheld, wherein the housing is configured to receive first and second printable materials from respective first and second containers;
 a mixer that is configured to mix the respective first and second materials from the first and second containers to form a mixture having a predetermined cross sectional structure having
  a plurality of discrete regions, each region defined by one of the first material or the second printable material, wherein the mixer comprises a plurality of helical mixing elements that are sequentially positioned longitudinally along the mixer, wherein each mixing element of the plurality of mixing elements has a flat leading edge and a flat trailing edge, wherein adjacent mixing elements of the plurality of helical mixing elements are rotationally offset from each other;
 a nozzle in communication with the housing, wherein the nozzle defines an outlet of the multi-material printer; and
 at least one actuator that is configured to cause the first and second printable materials from the first and second containers to flow through the housing at respective constant rates,
 wherein the multi-material printer is configured to simultaneously extrude the first and second printable materials from the outlet of the nozzle.

2. The multi-material printer of claim 1, further comprising the first and second containers, each having the respective first or second printable materials therein, wherein at least one of the first printable material or the second printable material comprises a biomaterial.

3. The multi-material printer of claim 2, wherein the first and second containers are coupled to the housing by a flexible conduit.

4. The multi-material printer of claim 2, wherein the first and second containers are received at least partially within the housing.

5. The multi-material printer of claim 2, wherein the first and second containers are configured to be received within the housing, wherein each of the first and second containers comprises:
 a longitudinal axis; and
 a plunger that is movable along the longitudinal axis, wherein the at least one actuator is configured to move the plunger of each container along the respective longitudinal axis of the container at a constant linear rate.

6. The multi-material printer of claim 2, wherein the first container comprises a first plunger and the second container comprises a second plunger, wherein the at least one actuator comprises a first actuator that is configured to actuate the plunger of the first container and a second actuator that is configured to actuate the plunger of the second container.

7. The multi-material printer of claim 6, wherein the first and second actuators are independently controllable to cause the plungers of the at least two syringes to move at different linear rates.

8. The multi-material printer of claim 1, wherein the multi-material printer is configured to print a filament comprising a plurality of linear compartments.

9. The multi-material printer of claim 1, wherein the mixer and nozzle are unitarily formed as a monolithic component.

10. The multi-material printer of claim 1, further comprising a radiation source that is configured to emit light for crosslinking hydrogel that has exited the nozzle.

11. The multi-material printer of claim 1, wherein the predetermined cross sectional structure of the mixture that the mixer is configured to form comprises a plurality of striations of the first and second materials.

12. The multi-material printer of claim 1, wherein the plurality of helical mixing elements have a generally helicoid shape with a 180 degree twist between opposite leading and trailing edges.

13. The multi-material printer of claim 1, wherein the plurality of discrete regions of the predetermined cross sectional structure comprises at least four discrete regions.

14. The multi-material printer of claim 1, wherein the plurality of mixing elements comprise a leading mixing element and a trailing mixing element, wherein each helical mixing element of the plurality of mixing elements has a length between the leading edge and the trailing edge of said helical mixing element, wherein the plurality of mixing elements cooperate to define a cumulative length between the leading edge of the leading mixing element and the trailing edge of the trailing mixing element, wherein the plurality of mixing elements are arranged end-to-end so that the cumulative length is substantially equal to a sum of the respective lengths of the plurality of mixing elements.

15. A method comprising:
 extruding, from the first and second containers of the multi-material printer of claim 4, first and second biomaterials, wherein the first biomaterial is within the first container, and wherein the second biomaterial is within the second container;
 mixing, with the mixer, the first and second biomaterials to form a mixture having a predetermined cross sectional structure having a plurality of discrete regions, each region defined by one of the first biomaterial or the second biomaterial; and
 depositing, through a nozzle, the mixture to form a filament.

16. The method of claim 15, wherein depositing the mixture to form the filament comprises depositing the mixture on or within a body of a patient.

17. The method of claim 15, wherein the predetermined cross sectional structure comprises linear striations of the first and second materials.

18. The method of claim 15, wherein the mixer comprises a plurality of helical mixing elements that are longitudinally spaced along the mixer, wherein adjacent mixing elements of the plurality of mixing elements are rotationally offset from each other.

19. The method of claim 15, wherein the nozzle and the mixer are components of a bioprinter, wherein the bioprinter comprises:
 a housing that is configured to be handheld, wherein the housing receives the first and second biomaterials from the first and second containers, wherein the nozzle is in communication with the housing; and
 at least one actuator that causes the first and second biomaterials from the first and second containers to flow through the housing,
 wherein the at least one actuator causes the first and second biomaterials to flow through the housing at respective constant rates.

* * * * *